United States Patent
Khairkhahan et al.

(10) Patent No.: US 8,377,114 B2
(45) Date of Patent: Feb. 19, 2013

(54) SEALING AND FILLING VENTRICULAR PARTITIONING DEVICES TO IMPROVE CARDIAC FUNCTION

(75) Inventors: Alexander Khairkhahan, Palo Alto, CA (US); Serjan D. Nikolic, Los Altos, CA (US); James R. Kermode, Los Altos, CA (US)

(73) Assignee: Cardiokinetix, Inc., Menlo Park, CA (US)

( * ) Notice: Subject to any disclaimer, the term of this patent is extended or adjusted under 35 U.S.C. 154(b) by 852 days.

(21) Appl. No.: 12/422,177

(22) Filed: Apr. 10, 2009

(65) Prior Publication Data

US 2010/0262168 A1 Oct. 14, 2010

(51) Int. Cl.
*A61F 2/06* (2006.01)
(52) U.S. Cl. .......... 623/1.23; 600/16; 600/37; 606/200; 604/508
(58) Field of Classification Search ............ 600/16, 600/37, 375; 604/508; 606/200, 213, 232; 623/23.67, 3.16, 1.11
See application file for complete search history.

(56) References Cited

U.S. PATENT DOCUMENTS

| | | | |
|---|---|---|---|
| 3,874,388 A | 4/1975 | King et al. | |
| 4,007,743 A | 2/1977 | Blake | |
| 4,425,908 A | 1/1984 | Simon | |
| 4,453,545 A | 6/1984 | Inoue | |
| 4,536,893 A | 8/1985 | Parravicini | |
| 4,588,404 A | 5/1986 | Lapeyre | |
| 4,619,246 A | 10/1986 | Molgaard-Nielsen et al. | |
| 4,685,446 A | 8/1987 | Choy | |
| 4,710,192 A | 12/1987 | Liotta et al. | |
| 4,832,055 A | 5/1989 | Palestrant | |
| 4,917,089 A | 4/1990 | Sideris | |
| 5,104,399 A | 4/1992 | Lazarus | |
| 5,192,301 A | 3/1993 | Kamiya et al. | |

(Continued)

FOREIGN PATENT DOCUMENTS

JP 2003512128 4/2003
JP 2003512129 4/2003

(Continued)

OTHER PUBLICATIONS

Khairkhahan Alexander; U.S. Appl. No. 13/129,961 entitled "Devices and methods for delivering an endocardial device," filed Jul. 14, 2011.

(Continued)

*Primary Examiner* — Vy Q Bui
(74) *Attorney, Agent, or Firm* — Shay Glenn, LLP

(57) ABSTRACT

Described herein are partitioning devices for reducing ventricular volume that may be secured within a ventricle and separate it into a productive portion and a non-productive portion. The partitioning devices described herein may include a reinforced membrane and may be secured within the heart chamber by sealing them to the wall of the heart chamber, for example, by inflating an inflatable element on the periphery of the device. All or a region of the non-productive portion formed by these devices may be enclosed within a container or bag. The non-productive portion may be filled with a material, including occlusive materials (e.g., vasoclusive coils). Sealing and/or filling the non-productive portion formed by the devices described herein may help prevent leakage from the non-productive region. Also described herein are systems including these devices and methods of using them, which may be suitable for treating patients with heart disease, particularly congestive heart failure.

12 Claims, 33 Drawing Sheets

U.S. PATENT DOCUMENTS

| | | |
|---|---|---|
| 5,192,314 A | 3/1993 | Daskalakis |
| 5,375,612 A | 12/1994 | Cottenceau et al. |
| 5,385,156 A | 1/1995 | Oliva |
| 5,389,087 A | 2/1995 | Miraki |
| 5,425,744 A | 6/1995 | Fagan et al. |
| 5,433,727 A | 7/1995 | Sideris |
| 5,451,235 A | 9/1995 | Lock et al. |
| 5,496,277 A | 3/1996 | Termin et al. |
| 5,527,337 A | 6/1996 | Stack et al. |
| 5,527,338 A | 6/1996 | Purdy |
| 5,549,621 A | 8/1996 | Bessler et al. |
| 5,578,069 A | 11/1996 | Miner, II |
| 5,634,936 A | 6/1997 | Linden et al. |
| 5,634,942 A | 6/1997 | Chevillon et al. |
| 5,647,870 A | 7/1997 | Kordis et al. |
| 5,702,343 A | 12/1997 | Alferness |
| 5,709,707 A | 1/1998 | Lock et al. |
| 5,791,231 A | 8/1998 | Cohn et al. |
| 5,797,849 A | 8/1998 | Vesely et al. |
| 5,797,960 A | 8/1998 | Stevens et al. |
| 5,800,457 A | 9/1998 | Gelbfish |
| 5,829,447 A | 11/1998 | Stevens et al. |
| 5,833,698 A | 11/1998 | Hinchliffe et al. |
| 5,836,968 A | 11/1998 | Simon et al. |
| 5,843,170 A | 12/1998 | Ahn |
| 5,860,951 A | 1/1999 | Eggers et al. |
| 5,861,003 A | 1/1999 | Latson et al. |
| 5,865,730 A | 2/1999 | Fox et al. |
| 5,865,791 A | 2/1999 | Whayne et al. |
| 5,871,017 A | 2/1999 | Mayer |
| 5,875,782 A | 3/1999 | Ferrari et al. |
| 5,876,325 A | 3/1999 | Mizuno et al. |
| 5,876,449 A | 3/1999 | Starck et al. |
| 5,879,366 A | 3/1999 | Shaw et al. |
| 5,882,340 A | 3/1999 | Yoon |
| 5,910,150 A | 6/1999 | Saadat |
| 5,916,145 A | 6/1999 | Chu et al. |
| 5,924,424 A | 7/1999 | Stevens et al. |
| 5,925,062 A | 7/1999 | Purdy |
| 5,925,076 A | 7/1999 | Inoue |
| 5,928,260 A | 7/1999 | Chin et al. |
| 5,961,440 A | 10/1999 | Schweich, Jr. et al. |
| 5,961,539 A | 10/1999 | Northrup, III et al. |
| 5,984,917 A | 11/1999 | Fleischman et al. |
| 6,024,096 A | 2/2000 | Buckberg |
| 6,024,756 A | 2/2000 | Huebsch et al. |
| 6,036,720 A | 3/2000 | Abrams et al. |
| 6,045,497 A | 4/2000 | Schweich, Jr. et al. |
| 6,059,715 A | 5/2000 | Schweich, Jr. et al. |
| 6,076,013 A | 6/2000 | Brennan et al. |
| 6,077,214 A | 6/2000 | Mortier et al. |
| 6,077,218 A | 6/2000 | Alferness |
| 6,093,199 A | 7/2000 | Brown et al. |
| 6,095,968 A | 8/2000 | Snyders |
| 6,096,347 A | 8/2000 | Geddes et al. |
| 6,099,832 A | 8/2000 | Mickle et al. |
| 6,102,887 A | 8/2000 | Altman |
| 6,125,852 A | 10/2000 | Stevens et al. |
| 6,132,438 A | 10/2000 | Fleischman et al. |
| 6,142,973 A | 11/2000 | Carleton et al. |
| 6,152,144 A * | 11/2000 | Lesh et al. .................. 128/898 |
| 6,156,027 A | 12/2000 | West |
| 6,161,543 A | 12/2000 | Cox et al. |
| 6,193,731 B1 | 2/2001 | Oppelt et al. |
| 6,221,092 B1 | 4/2001 | Koike et al. |
| 6,231,561 B1 | 5/2001 | Frazier et al. |
| 6,258,021 B1 | 7/2001 | Wilk |
| 6,267,772 B1 | 7/2001 | Mulhauser et al. |
| 6,290,674 B1 | 9/2001 | Roue et al. |
| 6,296,656 B1 | 10/2001 | Bolduc et al. |
| 6,312,446 B1 | 11/2001 | Huebsch et al. |
| 6,328,727 B1 | 12/2001 | Frazier et al. |
| 6,334,864 B1 | 1/2002 | Amplatz et al. |
| 6,343,605 B1 | 2/2002 | Lafontaine |
| 6,348,068 B1 | 2/2002 | Campbell et al. |
| 6,355,052 B1 | 3/2002 | Neuss et al. |
| 6,360,749 B1 | 3/2002 | Jayaraman |
| 6,364,896 B1 | 4/2002 | Addis |
| 6,387,042 B1 | 5/2002 | Herrero |
| 6,406,420 B1 | 6/2002 | McCarthy et al. |
| 6,419,669 B1 | 7/2002 | Frazier et al. |
| 6,436,088 B2 | 8/2002 | Frazier et al. |
| 6,450,171 B1 | 9/2002 | Buckberg et al. |
| 6,482,228 B1 | 11/2002 | Norred |
| 6,506,204 B2 | 1/2003 | Mazzocchi |
| 6,511,496 B1 | 1/2003 | Huter et al. |
| 6,537,198 B1 | 3/2003 | Vidlund et al. |
| 6,551,303 B1 | 4/2003 | Van Tassel et al. |
| 6,572,643 B1 | 6/2003 | Gharibadeh |
| 6,592,608 B2 | 7/2003 | Fisher et al. |
| 6,645,199 B1 | 11/2003 | Jenkins et al. |
| 6,652,555 B1 | 11/2003 | Van Tassel et al. |
| 6,685,627 B2 | 2/2004 | Jayaraman |
| 6,730,108 B2 | 5/2004 | Van Tassel et al. |
| 6,776,754 B1 | 8/2004 | Wilk |
| 6,852,076 B2 | 2/2005 | Nikolic et al. |
| 6,887,192 B1 | 5/2005 | Whayne et al. |
| 6,959,711 B2 | 11/2005 | Murphy et al. |
| 6,994,093 B2 | 2/2006 | Murphy et al. |
| 7,144,363 B2 | 12/2006 | Pai et al. |
| 7,320,665 B2 | 1/2008 | Vijay |
| 7,399,271 B2 | 7/2008 | Sharkey et al. |
| 7,569,062 B1 | 8/2009 | Kuehn et al. |
| 2001/0014800 A1 | 8/2001 | Frazier et al. |
| 2002/0019580 A1 | 2/2002 | Lau et al. |
| 2002/0026092 A1 | 2/2002 | Buckberg et al. |
| 2002/0028981 A1 | 3/2002 | Lau et al. |
| 2002/0032481 A1 | 3/2002 | Gabbay |
| 2002/0055767 A1 | 5/2002 | Forde et al. |
| 2002/0055775 A1 | 5/2002 | Carpentier et al. |
| 2002/0111647 A1 | 8/2002 | Khairkhahan et al. |
| 2002/0133227 A1 | 9/2002 | Murphy et al. |
| 2002/0161392 A1 | 10/2002 | Dubrul |
| 2002/0161394 A1 | 10/2002 | Macoviak et al. |
| 2002/0169359 A1 | 11/2002 | McCarthy et al. |
| 2002/0169360 A1 | 11/2002 | Taylor et al. |
| 2002/0188170 A1 | 12/2002 | Santamore et al. |
| 2003/0045896 A1 | 3/2003 | Murphy et al. |
| 2003/0050682 A1 | 3/2003 | Sharkey et al. |
| 2003/0050685 A1 | 3/2003 | Nikolic et al. |
| 2003/0105384 A1 | 6/2003 | Sharkey et al. |
| 2003/0109770 A1 | 6/2003 | Sharkey et al. |
| 2003/0120337 A1 | 6/2003 | Van Tassel et al. |
| 2003/0149333 A1 | 8/2003 | Alferness |
| 2003/0149422 A1 | 8/2003 | Muller |
| 2003/0181942 A1 | 9/2003 | Sutton et al. |
| 2003/0220667 A1 | 11/2003 | van der Burg et al. |
| 2004/0002626 A1 | 1/2004 | Feld et al. |
| 2004/0034366 A1 | 2/2004 | van der Burg et al. |
| 2004/0044361 A1 | 3/2004 | Frazier et al. |
| 2004/0054394 A1 | 3/2004 | Lee |
| 2004/0064014 A1 | 4/2004 | Melvin et al. |
| 2004/0127935 A1 | 7/2004 | Van Tassel et al. |
| 2004/0172042 A1 | 9/2004 | Suon et al. |
| 2004/0260331 A1 | 12/2004 | D'Aquanni et al. |
| 2004/0267378 A1 | 12/2004 | Gazi et al. |
| 2005/0007031 A1 | 1/2005 | Hyder |
| 2005/0015109 A1 | 1/2005 | Lichtenstein |
| 2005/0038470 A1 | 2/2005 | van der Burg et al. |
| 2005/0065548 A1 | 3/2005 | Marino et al. |
| 2005/0085826 A1 | 4/2005 | Nair et al. |
| 2005/0096498 A1 | 5/2005 | Houser et al. |
| 2005/0113861 A1 | 5/2005 | Corcoran et al. |
| 2005/0137690 A1 | 6/2005 | Salahieh et al. |
| 2005/0177180 A1 | 8/2005 | Kaganov et al. |
| 2005/0197716 A1 | 9/2005 | Sharkey et al. |
| 2005/0216052 A1 | 9/2005 | Mazzocchi et al. |
| 2005/0228434 A1 | 10/2005 | Amplatz et al. |
| 2005/0283218 A1 | 12/2005 | Williams |
| 2006/0014998 A1 | 1/2006 | Sharkey et al. |
| 2006/0025800 A1 | 2/2006 | Suresh |
| 2006/0030881 A1 | 2/2006 | Sharkey et al. |
| 2006/0116692 A1 | 6/2006 | Ward |
| 2006/0199995 A1 | 9/2006 | Vijay |
| 2006/0229491 A1 | 10/2006 | Sharkey et al. |
| 2006/0259124 A1 | 11/2006 | Matsuoka et al. |
| 2006/0264980 A1 | 11/2006 | Khairkhahan et al. |

| | | |
|---|---|---|
| 2006/0276684 A1 | 12/2006 | Speziali |
| 2006/0281965 A1 | 12/2006 | Khairkhahan et al. |
| 2007/0129753 A1 | 6/2007 | Quinn et al. |
| 2007/0135889 A1 | 6/2007 | Moore et al. |
| 2007/0161846 A1 | 7/2007 | Nikolic et al. |
| 2007/0162048 A1 | 7/2007 | Quinn et al. |
| 2007/0213578 A1 | 9/2007 | Khairkhahan et al. |
| 2007/0213815 A1 | 9/2007 | Khairkhahan et al. |
| 2008/0015717 A1 | 1/2008 | Griffin et al. |
| 2008/0045778 A1 | 2/2008 | Lichtenstein et al. |
| 2008/0071298 A1 | 3/2008 | Khairkhahan et al. |
| 2008/0228205 A1 | 9/2008 | Khairkhahan et al. |
| 2008/0293996 A1 | 11/2008 | Evans et al. |
| 2008/0319254 A1 | 12/2008 | Nikolic et al. |
| 2009/0054723 A1 | 2/2009 | Khairkhahan et al. |
| 2009/0062601 A1 | 3/2009 | Khairkhahan et al. |
| 2009/0254195 A1 | 10/2009 | Khairkhahan et al. |
| 2009/0287040 A1 | 11/2009 | Khairkhahan et al. |
| 2010/0121132 A1 | 5/2010 | Nikolic et al. |
| 2010/0274227 A1 | 10/2010 | Khairkhahan et al. |

FOREIGN PATENT DOCUMENTS

| | | |
|---|---|---|
| WO | WO 00/27292 | 5/2000 |
| WO | WO 01/30266 | 5/2001 |
| WO | WO 01/78625 | 10/2001 |
| WO | WO 02/30335 | 4/2002 |
| WO | WO 02/071977 A2 | 9/2002 |
| WO | WO 03/007778 | 1/2003 |
| WO | WO 03/073961 A1 | 9/2003 |
| WO | WO 2004/012629 | 2/2004 |
| WO | WO 2004/100803 A1 | 11/2004 |
| WO | WO 2005/007031 | 1/2005 |
| WO | WO 2007/092354 | 8/2007 |

OTHER PUBLICATIONS

Boersma et al.; Early thrombolytic treatment in acute myocardial infarction: reappraisal of the golden hour; Lancet: vol. 348; pp. 771-775; 1996.

Khairkhahan, Alexander; U.S. Appl. No. 12/181,282 entitled "Inflatable ventricular partitioning device," filed Jul. 28, 2008.

Khairkhahan et al; U.S. Appl. No. 12/198,022 entitled "Retrievable cardiac devices," filed Aug. 25, 2008.

AGA Medical Corporation. www.amplatzer.com/products. "The Muscular VSD Occluder" and "The Septal Occluder" device description. Accessed Apr. 3, 2002.

Di Mattia, et al. Surgical treatment of left ventricular post-infarction aneurysm with endoventriculoplasty: late clinical and functioal results. European Journal of Cardio-thoracic Surgery. 1999; 15:413-418.

Dor, et al. Ventricular remodeling in coronary artery disease. Current Opinion in Cardiology. 1997; 12:533-537.

Dor, V. The treatment of refractory ischemic ventricular tachycardia by endoventricular patch plasty reconstruction of the left ventricle. Seminars in Thoracic and Cardiovascular Surgery. 1997; 9(2): 146-155.

Dor. Surgery for left ventricular aneurysm. Current Opinion in Cardiology. 1990; 5: 773-780.

Gore Medical. www.goremedical.com. "Helex Septal Occluder" product description. Accessed Apr. 3, 2002.

Katsumata, et al. An objective appraisal of partial left ventriculectomy for heart failure. Journal of Congestive Heart Failure and Circulator Support. 1999; 1(2): 97-106.

Kawata, et al. Systolic and Diastolic Function after Patch Reconstruction of Left Ventricular Aneurysms. Ann. Thorac. Surg. 1995; 59:403-407.

James et al.; Blood Volume and Brain Natriuretic Peptide in Congestive Heart Failure: A Pilot Study; American Heart Journal; vol. 150; issue 5, pp. 984.e1-984.e6 (abstract); Dec. 6, 2005.

Boutillette et al.; U.S. Appl. No. 12/893,832 entitled "Devices and methods for delivering an endocardial device," filed Sep. 29, 2010.

Kermode et al.; U.S. Appl. No. 12/912,632 entitled "Ventrical volume reduction," filed Oct. 26, 2010.

Artrip et al.; Left ventricular volume reduction surgery for heart failure: A physiologic perspective; J Thorac Cardiovasc Surg; vol. 122; No. 4; pp. 775-782; 2001.

Januzzi, James L.; Natriuretic peptide testing: A window into the diagnosis and prognosis of heart failure; Cleveland Clinic Journal of Medicine; vol.73; No. 2; pp. 149-152 and 155-157; Feb. 2006.

* cited by examiner

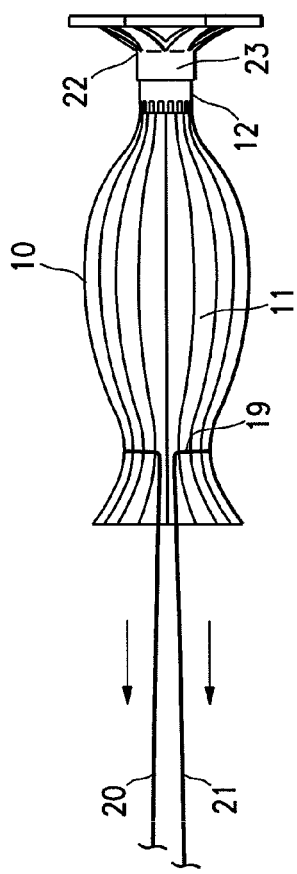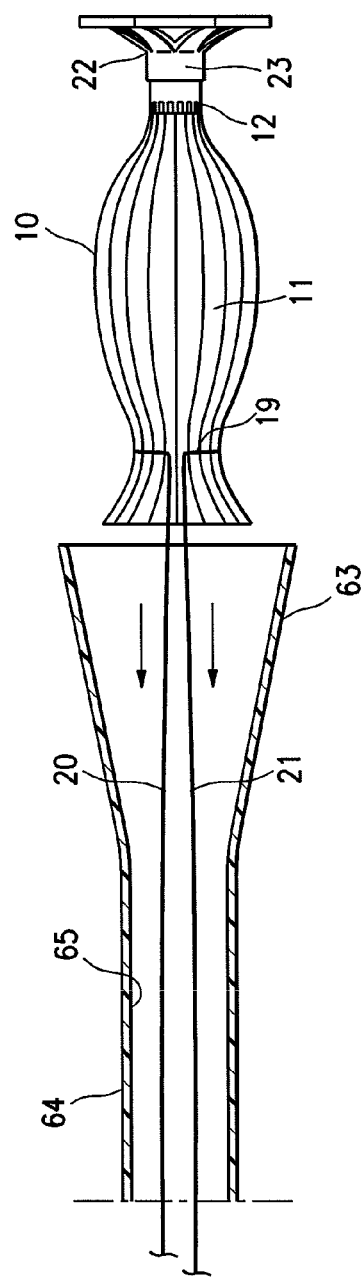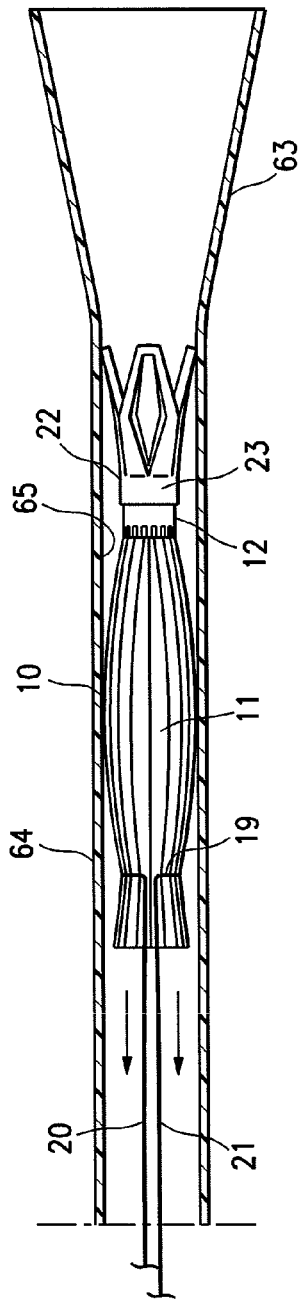

VALVE OPEN

VALVE CLOSED

SEALING AND FILLING VENTRICULAR PARTITIONING DEVICES TO IMPROVE CARDIAC FUNCTION

CROSS REFERENCE TO RELATED APPLICATIONS

None.

This application may be related to U.S. patent application Ser. No. 10/436,959, titled "System for Improving Cardiac Function", filed May 12, 2003, and U.S. patent application Ser. No. 11/151,164, titled "Peripheral Seal for a Ventricular Partitioning Device," filed Jun. 10, 2005.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

The devices, systems and methods described herein relate generally to the treatment of heart disease, particularly congestive heart failure, and more specifically, to devices, systems and methods for partitioning a patient's heart chamber and a system for delivering the treatment device.

BACKGROUND OF THE INVENTION

Congestive heart failure (CHF) is characterized by a progressive enlargement of the heart, particularly the left ventricle and is a major cause of death and disability in the United States. Approximately 550,000 new cases occur annually in the U.S. alone. As the patient's heart enlarges, it cannot efficiently pump blood forward with each heart beat. In time, the heart becomes so enlarged the heart becomes ineffective as a pump and cannot adequately supply blood to the body. Even in healthy hearts only a certain percentage of the blood in a patient's left ventricle is pumped out or ejected from the chamber during each stroke of the heart. The pumped percentage, commonly referred to as the "ejection fraction", is typically about sixty percent for a healthy heart. A patient with congestive heart failure can have an ejection fraction of less than 40% and sometimes much lower. As a result of the low ejection fraction, a patient with congestive heart failure is fatigued, unable to perform even simple tasks requiring exertion and experiences pain and discomfort. Further, as the heart enlarges, the internal heart valves such as the mitral valve cannot adequately close. An incompetent mitral valve allows regurgitation of blood from the left ventricle back into the left atrium, further reducing the heart's ability to pump blood forwardly.

Congestive heart failure can result from a variety of conditions, including viral infections, incompetent heart valves (e.g. mitral valve), ischemic conditions in the heart wall or a combination of these conditions. Prolonged ischemia and occlusion of coronary arteries can result in myocardial tissue in the ventricular wall dying and becoming scar tissue. Once the myocardial tissue dies, it is less contractile (sometimes non-contractile) and no longer contributes to the pumping action of the heart. It is referred to as hypokinetic or akinetic. As the disease progresses, a local area of compromised myocardium may bulge out during the heart contractions, further decreasing the heart's ability to pump blood and further reducing the ejection fraction. In this instance, the heart wall is referred to as dyskinetic. The dyskinetic region of the heart wall may stretch and eventually form an aneurysmic bulge.

Patients suffering from congestive heart failure are commonly grouped into four classes, Classes I, II, III and IV. In the early stages, Classes I and II, drug therapy is presently the most common treatment. Drug therapy typically treats the symptoms of the disease and may slow the progression of the disease, but it cannot cure the disease. Presently, the only permanent treatment for congestive heart disease is heart transplantation, but heart transplant procedures are very risky, extremely invasive and expensive and are performed on a small percentage of patients. Many patient's do not qualify for heart transplant for failure to meet any one of a number of qualifying criteria, and, furthermore, there are not enough hearts available for transplant to meet the needs of CBF patients who do qualify.

Substantial effort has been made to find alternative treatments for congestive heart disease. For example, surgical procedures have been developed to dissect and remove weakened portions of the ventricular wall in order to reduce heart volume. This procedure is highly invasive, risky and expensive and is commonly only done in conjunction with other procedures (such as heart valve replacement or coronary artery by-pass graft). Additionally, the surgical treatment is usually only offered to Class III and IV patients and, accordingly, is not an option for most patients facing ineffective drug treatment. Finally, if the procedure fails, emergency heart transplant is the only presently available option.

Mechanical assist devices have been developed as intermediate procedures for treating congestive heart disease. Such devices include left ventricular assist devices and total artificial hearts. A left ventricular assist device includes a mechanical pump for increasing blood flow from the left ventricle into the aorta. Total artificial heart devices, such as the Jarvik heart, are usually used only as temporary measures while a patient awaits a donor heart for transplant.

Recently, improvements have been made in treating patients with CHF by implanting pacing leads in both sides of the heart in order to coordinate the contraction of both ventricles of the heart. This technique has been shown to improve hemodynamic performance and can result in increased ejection fraction from the right ventricle to the patient's lungs and the ejection fraction from the left ventricle to the patient's aorta. While this procedure has been found to be successful in providing some relief from CHF symptoms and slowed the progression of the disease, it has not been able to stop the disease and is only indicated in patients with ventricular dissynchrony.

Other efforts to treat CHF include the use of an elastic support, such as an artificial elastic sock, placed around the heart to prevent further deleterious remodeling.

Described herein are ventricular partitioning devices that address many of the problems associated with devices that reduce heart volume or modify cardiac contraction. In particular, the devices, systems and methods described herein may reduce volume in a ventricle in a way that avoids leakage or the release of potentially thrombogenic materials.

SUMMARY OF THE INVENTION

The present invention is directed to ventricular partitioning devices, systems and methods of employing ventricular partitioning devices in the treatment of a patient with heart disease and particularly congestive heart failure (CHF). Specifically, the devices described herein partition a chamber of the patient's heart into a main productive portion and a secondary non-productive portion, and form a seal between the two portions. In some variations, the devices include a separate chamber that is configured to fit within the non-productive portion. Partitioning reduces the total volume of the heart chamber, reduces the stress applied to weakened tissue of the patient's heart wall and, as a result, improves the ejection fraction thereof. Moreover, the expansive nature of the device improves the diastolic function of the patient's heart.

In general, the partitioning devices described herein have a reinforced partitioning component with a concave, pressure receiving surface which defines in part the main productive portion of the partitioned heart chamber when secured within the patient's heart chamber. The reinforced partitioning component may include a flexible membrane that forms the pressure receiving surface. The partitioning component may be reinforced by a radially expandable frame component formed of a plurality of ribs. The ribs of the expandable frame may have secured distal ends, which are preferably secured to a central hub, and free proximal ends. The distal ends of the ribs may be secured to the central hub to facilitate radial self expansion of the free proximal ends of the ribs away from a centerline axis. The distal ends of the ribs may be pivotally mounted to the hub and biased outwardly or fixed to the hub. The ribs are preferably formed of material such as superelastic NiTi alloy which allows for compressing the free proximal ends of the ribs toward a centerline axis into a contracted configuration for delivery and self-expansion when released for deployment to an expanded configuration when released within the patient's heart chamber.

The free ends of the ribs may be configured to engage and preferably penetrate the tissue lining the heart chamber to be partitioned so as to secure the peripheral edge of the partitioning component to the heart wall and fix the partitioning component within the chamber so as to partition the chamber in a desired manner. The tissue penetrating proximal tips may be configured to penetrate the tissue lining at an angle approximately perpendicular to a center line axis of the partitioning device. The tissue penetrating proximal tips of the ribs may be provided with barbs, hooks and the like which prevent withdrawal from the tips from the heart wall.

The portioning devices described herein may also include a sealing element (or sealing elements) configured to seal the device (which may be separately secured to the heart wall) to the heart wall. For example, the device may include an expansive member such as one or more strands, swellable pads, inflatable balloons, or the like, that extend between at least one pair of adjacent ribs at or close to the outer edge or periphery of the membrane to seal the membrane to the heart wall. For example, the sealing element may exert pressure to the flexible membrane periphery when the partitioning device is in an expanded configuration to ensure an adequate seal between the membrane periphery and the lining of the heart wall. In one embodiment, a single strand or strands extend around essentially the entire periphery of the membrane so that the flexible periphery of the membrane between each pair of ribs is effectively sealed against the heart wall. The expansive strand or strands may be formed of material which is stiffer than the flexible, unsupported material of the membrane to provide an outward expansive force or thrust to prevent formation of inwardly directed folds or wrinkles when the ribs of the partitioning device are in at least a partially contracted configuration. Suitable strand or strands are formed of material such as polypropylene suture or superelastic NiTi alloy wires. Such strands may typically be about 0.005 to about 0.03 inch (0.13-0.76 mm) in diameter to provide the requisite outward expansive force when placed in a circular position such as around the periphery of the membrane in less than completely expanded configuration.

In another embodiment expandable pads are provided between each adjacent pair of ribs which are configured to swell upon contact with body fluids to provide an outward expansive force or thrust, as above, to prevent formation of inwardly directed folds or wrinkles when the ribs of the partitioning device are in at least a partially contracted configuration. Preferably the pads are formed of expansive hydrophilic foam. Suitable swellable materials includable collagen, gelatin, polylactic acid, polyglycolic acid, copolymers of polylactic acid and polyglycolic acid, polycaprolactone, mixtures and copolymers thereof. Other suitable swellable bioresorbable polymeric materials may be employed. The expandable pads may be formed so as to deliver a variety of therapeutic or diagnostic agents.

In some variations, the ribs in their expanded configuration typically angle outwardly from the hub and the free proximal ends curve outwardly so that the membrane secured to the ribs of the expanded frame forms a trumpet-shaped, pressure receiving surface.

The partitioning membrane in the expanded configuration may have radial dimensions from about 10 to about 160 mm, preferably about 25 to about 50 mm, as measured from the center line axis. The membrane is preferably formed of flexible material or fabric such as expanded polytetrafluoroethylene (ePTFE).

The partitioning device may be designed to be oversized with respect to the chamber in which it is to be deployed so that the ribs of the device apply an outward force against the chamber wall. When the partitioning device is collapsed for delivery, the outwardly biased strand or strands ensures that there are no inwardly directed folds or wrinkles and that none are formed when the partitioning device is expanded for deployment within the heart chamber.

In one partitioning device design, the free ends of the expansive strand or strands may be secured together or to the partitioning device. Alternatively, in another device design, the expansive strand or strands may be long enough so that one or both free ends thereof extend out of the patient to facilitate collapse and retrieval of the partitioning device. Pulling on the free ends of the strand extending out of the patient closes the expanded portion i.e. the ribs and membrane, of the partitioning device to collapse of the device and such pulling can pull the collapsed partitioning device into the inner lumen of a guide catheter or other collecting device The reinforced partitioning component may include a supporting component or stem which has a length configured to extend distally to the heart wall surface to support the partitioning device within the heart chamber. For example, the supporting component may have a plurality of pods or feet, preferably at least three, which distribute the force of the partitioning device about a region of the ventricular wall surface to avoid immediate or long term damage to the tissue of the heart wall, particularly compromised or necrotic tissue such as tissue of a myocardial infarct (MI) and the like. Pods of the support component may extend radially and preferably be interconnected by struts or planes which help distribute the force over an expanded area of the ventricular surface.

Any of the partitioning devices described herein may be delivered percutaneously or intraoperatively. Thus, methods of delivery and devices for delivering them are also described herein. For example, one delivery catheter which may be used has an elongated shaft, a releasable securing device on the distal end of the shaft for holding the partitioning device on the distal end and an expandable member such as an inflatable balloon on a distal portion of the shaft proximal to the distal end to press the interior of the recess formed by the pressure receiving surface to ensure that the tissue penetrating tips or elements on the periphery of the partitioning device penetrate sufficiently into the heart wall to hold the partitioning device in a desired position to effectively partition the heart chamber. For example, one variation of a suitable delivery device is described in co-pending application Ser. No. 10/913,608, filed on Aug. 5, 2004, and assigned to the present assignee.

For example, described herein are devices for partitioning a patient's ventricle into a productive portion and a non-productive portion, the device comprising: a membrane and a membrane support frame sized to span the patient's ventricle, wherein the membrane support frame comprises a plurality of support struts configured to have a collapsed and an expanded configuration; at least one securing element extending from the periphery of the membrane; and an inflatable sealing element on a peripheral portion of the membrane configured to seal the peripheral portion of the membrane to a wall of the ventricle.

In general, the inflatable sealing element includes swellable sealing elements. A swellable sealing element typically inflates from a smaller profile to a larger (swelled or inflated) profile. Any of the inflatable sealing elements described herein may be considered expansive members that expand in order to secure and/or seal the membrane of the devices against a wall of a heart chamber. In some variations, the inflatable sealing element extends annularly around the perimeter of the membrane. For example, the inflatable sealing element may be a plurality of inflatable sealing elements extending between the support struts.

The membrane support frame may be configured to form a recess in the expanded configuration.

Any of the devices described herein may also include a valve configured to allow access to the non-productive portion when the device is deployed in the subject's ventricle. In some variations, the valve comprises a one-way valve.

The membrane may be formed at least in part of a flexible material.

The devices described herein may also include an inflation valve fluidly connected to the inflatable sealing element.

The inflatable sealing element may be formed of any appropriate material, in particular, the inflatable sealing element may be formed of a bioabsorbable material. In some variations, the bioabsorbable material is selected from the group consisting of collagen, gelatin, polylactic acid, polyglycolic acid, copolymers of polylactic acid and polyglycolic acid, polycaprolactone, mixtures and copolymers thereof.

Any of the partitioning devices described herein may also include a central hub to which the membrane support frame is secured, and/or a stem with a non-traumatic distal tip configured to engage a region of the chamber defining in part the non-productive portion thereof. The securing elements may be anchors, and may be tissue penetrating. For example, the securing elements may have a tissue penetrating tip. The securing element(s) may be outwardly curved.

In some variations, the partitioning device may also include one or more containers secured to the device that may be filled once the device is inserted into the ventricle. For example, the device may include a container secured to the device and configured to be positioned within the non-productive portion of the subject's ventricle when the device is deployed in the subject's ventricle. The container may be a bag having flexible walls, or it may have rigid or semi-flexible walls. The container may be collapsed or foldable. In some variations the membrane connected to the support frame forms a wall or portion of the container. Thus, the container may extend from the membrane and/or support frame distally, so that it may be positioned within the non-productive portion of the ventricle when the device is deployed. Portions of the device may be contained within the container. For example, a stem portion, a foot portion, etc. may be positioned within the container. The container may be expandable. For example, the container may be a flexible or stretchable fabric. The container may be configured to hold a fluid or solid. Thus, in some variations the container is configured to be fluid-tight. In some variations the container may be filled with a fluid such as saline, blood, etc. In other variations, the container may be permeable or semi-permeable.

Also described herein are methods for treating a patient, including a patient having a heart disorder, or at risk for a heart disorder. The method may include the steps of: percutaneously advancing a contracted partitioning device into a patient's ventricle; expanding the partitioning device into a deployed configuration within the ventricle; and sealing the expanded partitioning component to the wall of the ventricle to separate the ventricle into a productive portion and a non-productive portion to prevent communication between the productive portion and non-productive portions.

The method may also include the step of filling the non-productive portion. For example, the non-productive portion may be filled with a bio-resorbable filler such as polylactic acid, polyglycolic acid, polycaprolactone and copolymers and blends. In some variations, the filler is an occlusive material such as a coil (e.g., vasoocclusive coil) or the like. Fillers may be suitably supplied in a suitable solvent such as dimethylsulfoxide (DMSO). Other materials which accelerate tissue growth or thrombus may be deployed in the non-productive portion, as well as non-reactive fillers.

The sealing step may include expanding a sealing element against the ventricle wall from the partitioning device. The sealing step may include the step of biasing a membrane toward the heart wall with the sealing element. For example, the expanding step may include inflating the sealing element. In some variations, the sealing element may be actively expanded (e.g., by applying air or other fluids), or passively expanded (e.g., by allowing swelling).

Also described herein are methods of treating a patient comprising the steps of: percutaneously advancing a contracted partitioning device into a patient's ventricle; expanding the partitioning device into a deployed configuration within the ventricle; securing the expanded partitioning device to the ventricle wall to separate the ventricle into a productive portion and a non-productive portion; and adding a filling material to the non-productive portion.

In some variations, the step of adding a filling material includes applying material through a valve on the partitioning device. The valve may be a one-way valve. The material may be applied through a channel in the applicator. For example, the applicator may engage with a valve on or through the device. In some variations, the device is passively filled. For example, one or more valves may allow the entry of blood flow behind the device, but may prevent the blood (or any thrombosis) from exiting the non-productive space behind the valve. Thus the step of adding the filing material may include passively allowing a blood to fill a compartment portion of the partitioning device through a valve on the device.

In some variations, the step of adding a filling material includes applying a filling material into a compartment portion of the partitioning device through a valve. As mentioned above the compartment may be filled with any appropriate filling material, including fluids, solids, or some combination thereof. For example, the step of adding a filling material may include applying one or more coils to the non-productive portion. The coils (e.g., vasooccluisve coils) or other filling material may be added to a compartment portion of the partitioning device. The step of adding the filing material may comprise applying saline to a compartment portion of the partitioning device.

Also described herein are applicators for applying a partitioning device of a ventricle of a patient's heart. An applicator may include: an elongated shaft which has proximal and distal ends; an deploying inflation port on the proximal end of the shaft and an inner lumen in fluid communication with the port; a releasable securing element on the distal end of the elongated shaft configured to secure and release the partitioning device; an inflatable member on a distal portion of the elongated shaft having an interior in fluid communication with the deploying inflation port, wherein the inflatable member is configured to expand a membrane of the partitioning device; and a filling interface near the distal end of the elongated shaft, wherein the filling interface is configured to apply a filling material through a valve on the partitioning device.

One particular variation of the devices for partitioning a patient's ventricle into a product and non-productive portion includes an inflatable sealing element that is a balloon element. For example, described herein are devices for partitioning a patient's ventricle into a productive portion and a non-productive portion. Such devices may include a membrane and a membrane support frame sized to span the patient's ventricle, wherein the membrane support frame comprises a plurality of support struts configured to have a collapsed and an expanded configuration, at least one securing element extending from the periphery of the membrane, and an inflatable sealing balloon element on a peripheral portion of the membrane configured to seal the peripheral portion of the membrane to a wall of the ventricle.

As mentioned above, the inflatable sealing balloon element may extend substantially around the perimeter of the membrane. In some variations, the partitioning devices include a plurality of inflatable sealing balloon elements extending between support struts.

A partitioning device may also include an inflation port configured to connect the inflatable sealing balloon element to a channel on a delivery device. The devices may also include an inflation valve fluidly connected to the inflatable sealing element.

As mentioned above, the securing element(s) of the partitioning device may have a tissue penetrating tip.

These partitioning devices may also include a container secured to the device and configured to be positioned within the non-productive portion of the subject's ventricle when the device is deployed in the patient's ventricle.

Also described herein are devices for partitioning a ventricle of a patient's heart into a productive portion and a non-productive portion that include: a membrane and a membrane support frame, the membrane and the membrane support frame sized to span the patient's ventricle, wherein the membrane and the membrane support frame are configured to have a collapsed configuration and an expanded configuration; at least one securing element on a peripheral portion of the membrane configured to secure the membrane to a wall of the ventricle; and a container secured to the device and configured to be positioned within the non-productive portion of the subject's ventricle when the device is deployed in the subject's ventricle. The container may be secured to the membrane. In some variations, the membrane forms a wall or portion of the container. The container may extend from a peripheral portion of the membrane.

The container may be configured to substantially conform to the ventricular wall. For example, the container may be fillable so that it contacts all or a portion of the ventricle wall in the non-productive portion of the ventricle. In some variations, the container is configured as a bag.

As mentioned above, the container may be expandable, or it may have a fixed volume. The container may be made of a flexible material. In some variations, the container comprises one or more rigid walls. The container may be permeable or impermeable. In general, the container may be fillable. For example, the container may be configured to be filled with a fluid. In some variations, the container is configured to be filled with one or more coils or other occlusive members. The devices described herein may include a valve providing access into the container. For example, the valve may be configured to permit filling, but not emptying of the container. Thus, in one variation the valve is a one-way valve configured to allow the container to passively fill with blood from the ventricle. In some variations, the container may be configured so that the valve can permit emptying.

Any of the features of the partitioning devices described herein may be included as part of the portioning devices including a container. For example, the devices may include a central hub, a stem, a foot (e.g., an atraumatic foot), or the like. In some variations the device may be configured so that one or more of these elements is contained within the container.

Also described herein are methods of treating a patient comprising: percutaneously advancing a contracted partitioning device into a patient's ventricle; expanding the partitioning device into a deployed configuration within the ventricle; sealing the expanded partitioning component to the wall of the ventricle to separate the ventricle into a productive portion and a non-productive portion to prevent communication between the productive portion and non-productive portions; and filling a container portion of the implant that is secured within the non-productive portion of the ventricle.

The step of filling may comprise filling the container portion with an occlusive device, or with some other solid and/or liquid material, e.g., saline.

Also described herein are applicators for applying a partitioning device to a ventricle of a patient's heart, the applicator comprising: an elongated shaft which has proximal and distal ends; a deploying inflation port and a sealing inflation port on the proximal end of the shaft; an inner lumen in fluid communication with at least one of the ports; a releasable securing element on the distal end of the elongated shaft configured to secure and release the partitioning device; an inflatable member on a distal portion of the elongated shaft having an interior in fluid communication with the deploying inflation port; and a sealing inflation interface near the distal end of the elongated shaft in fluid communication with the sealing inflation port, wherein the sealing inflation interface is configured to couple to an inflatable sealing element of the partitioning device.

Other variations of partitioning devices having one or more chambers are also described herein. For example, described herein are ventricular chamber volume reduction systems, comprising: a container body deliverable into a portion of a ventricular chamber, and wherein the container body is expandable from a first shape to a second shape when delivered into the ventricular chamber, the container body having a tissue surface in contact with a wall of the ventricular chamber and an exposed surface facing into the volume of the ventricular chamber not occupied by the container body, and wherein the exposed surface substantially spans across the ventricular chamber, wherein the second shape of the container body occupies substantially all of the space in the ventricular chamber between the wall of the portion of the ventricular chamber and the exposed surface, thereby reducing ventricular volume exposed to a flow of blood. In some variations, these devices also include a partition, wherein the partition is positioned on the side of the container adjacent to the exposed surface.

As mentioned above, the second shape of the container body may occupy substantially all of the space in the ventricular chamber between the wall of the portion of the ventricular chamber and the exposed surface. For example, when the device is filled with material, one or more walls of the device may contact the sides of the ventricle in the non-productive portion of the ventricle.

The container body may include an attachment device that affixes the tissue surface to the wall of the ventricular chamber. For example, the container body may include one or more anchors, hooks, barbs or the like. In some variations, the container body may include one or more struts or arms that apply pressure to secure the tissue surface to a wall of the ventricular chamber. In some variations the chamber body may be sealed against the wall of the ventricular chamber by expanding or inflating an inflatable member, as described above. The inflatable member may be present with the container. In some variations, the expandable member is present on the outside of the container. The container may also be expandable and/or inflatable.

A partitioning device embodying features of the invention may be relatively easy to install and may be a substantially improved treatment of a diseased heart. A more normal diastolic and systolic movement of a patient's diseased heart may thus be achieved. Concomitantly, an increase in the ejection fraction of the patient's heart chamber can be obtained. These and other advantages of the invention will become more apparent from the following detailed description of the invention and the accompanying exemplary drawings.

BRIEF DESCRIPTION OF THE DRAWINGS

FIG. 14 is a partial schematic view of the partitioning device shown in FIGS. 1 and 2 in a contracted configuration resulting from pulling the free ends of the expansive strand at the periphery of the reinforced membrane.

FIG. 15 is a schematic view of the contracted device shown in FIG. 14 being pulled into an expanded distal end of a receiving catheter to facilitate withdrawal of the partitioning device into a receiving catheter.

FIG. 16 is a schematic view of the contracted device shown in FIG. 14 pulled further into the inner lumen of the receiving catheter.

FIG. 21 shows the device in the collapsed (delivery) configuration, while FIG. 21B shows a partially expanded view. FIG. 21C shows a partial cut-away view of the device of FIGS. 21A and 21B.

DETAILED DESCRIPTION OF THE INVENTION

Partitioning devices, systems including partitioning devices, and methods of using partitioning devices to treat subjects are described herein. In general, the partitioning devices described herein are configured to partition a heart chamber, and in particular a ventricular chamber, into a productive portion and a non-productive portion. These partitioning devices may be delivered in a collapsed configuration (e.g., percutaneously), and expanded within the ventricle and secured in position within the ventricle, thereby partitioning it. The partitioning devices described herein both secure to the heart wall (e.g., by anchors, barbs, spikes, etc.) and also (and possibly separately) seal to the heart wall. Sealing to the wall of a heart chamber may be complicated or made difficult by the presence of trabeculations and wall irregularities. Thus, the devices described herein may include one or more sealing elements that are configured to help seal the device (e.g., the partitioning membrane of the device) to the heart wall.

The partitioning devices described herein may also be configured so that the non-productive region formed by the partitioning device may be filled after it is deployed. Filling the non-productive portion may prevent leak, and may also help secure the device in position. As described in detail below, any appropriate filling material may be used, including occlusive material such as coils, fluids (saline, blood, etc.), or the like.

Also described below are variations of partitioning devices that include one or more containers. A container may be referred to as a compartment, chamber, bag, or the like. Partitioning devices including containers may be deployed into the heart (e.g., in the ventricle), so that the container portion is within (or at least partially forms) the non-productive region. In some variations, portions of the partitioning device are contained within the container. The container may be filled or fillable, and may include one or more ports for filing. The ports may be valved, and may include one-way valves so that the container does not leak. Thus, the container may be fluid-tight. The container may be located distally to the pressure-receiving membrane of the device (which may form a portion or wall of the chamber), and may fill all or most of the non-productive space. In some variations the chamber includes anchors (e.g., hooks, barbs, adhesive, etc.) to secure the chamber to the wall of the ventricle. These anchors may be in addition to other anchors or securing elements on the device (e.g., around the perimeter of the pressure-receiving membrane).

Figure 1:
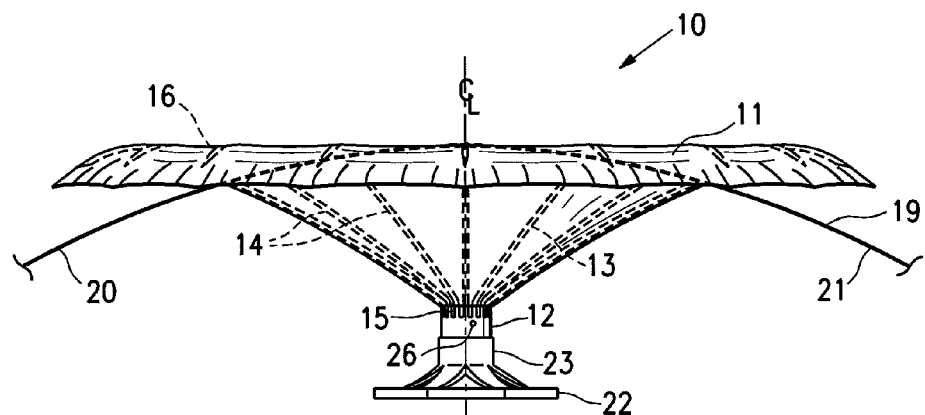
FIG. 1 is an elevational view of a partitioning device embodying features of the invention in an expanded configuration.

For example, FIGS. 1-4 illustrate one variations of a partitioning device 10 which includes a partitioning membrane (e.g., pressure-receiving membrane) 11, a hub 12, preferably centrally located on the partitioning device, and a radially expandable reinforcing frame 13 is secured to the proximal or pressure side of the frame 13 as shown in FIG. 1. The ribs 14 have distal ends 15 which are secured to the hub 12 and free proximal ends 16 which are configured to curve or flare away from a center line axis. Radial expansion of the free proximal ends 16 unfurls the membrane 11 secured to the frame 13 so that the membrane presents a pressure receiving surface 17 which defines in part the productive portion of the patient's partitioned heart chamber. The peripheral edge 18 of the membrane 11 may be serrated as shown.

In this example, the device includes a sealing element that is a continuous expansive strand 19 that extends around the periphery of the membrane 11 on the pressure side thereof to apply pressure to the pressure side of the flexible material of the membrane to effectively seal the periphery of the membrane against the wall of the ventricular chamber. The ends 20 and 21 of the expansive strand 19 are shown extending away from the partitioning device in FIGS. 2 and 3. The ends 20 and 21 may be left unattached or may be secured together, e.g. by a suitable adhesive or the membrane 11 itself. While not shown in detail, the membrane 11 has a proximal layer secured to the proximal faces of the ribs 14 and a distal layer secured to the distal faces of the ribs in a manner described in co-pending application Ser. No. 10/913,608, filed on Aug. 5, 2004.

Figure 4:
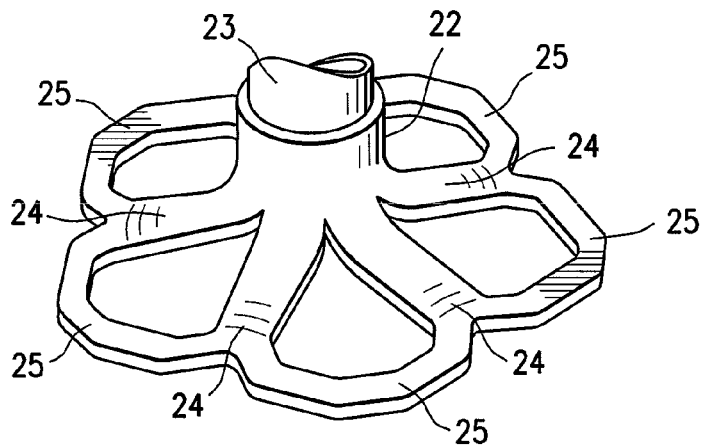
FIG. 4 is a perspective view of the non-traumatic tip of the distally extending stem of the device shown in FIG. 1.
Figure 5:
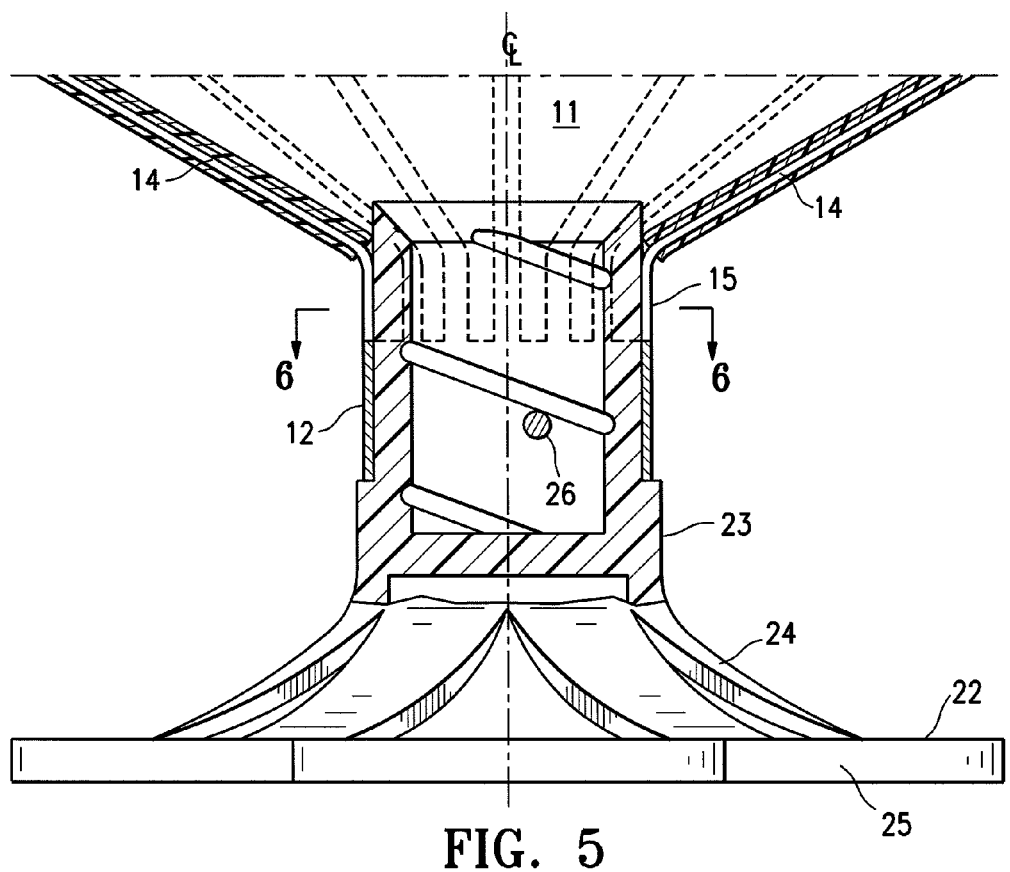
FIG. 5 is a partial cross-sectional view of the hub of the partitioning device shown in FIG. 2 taken along the lines 5-5.
Figure 8:
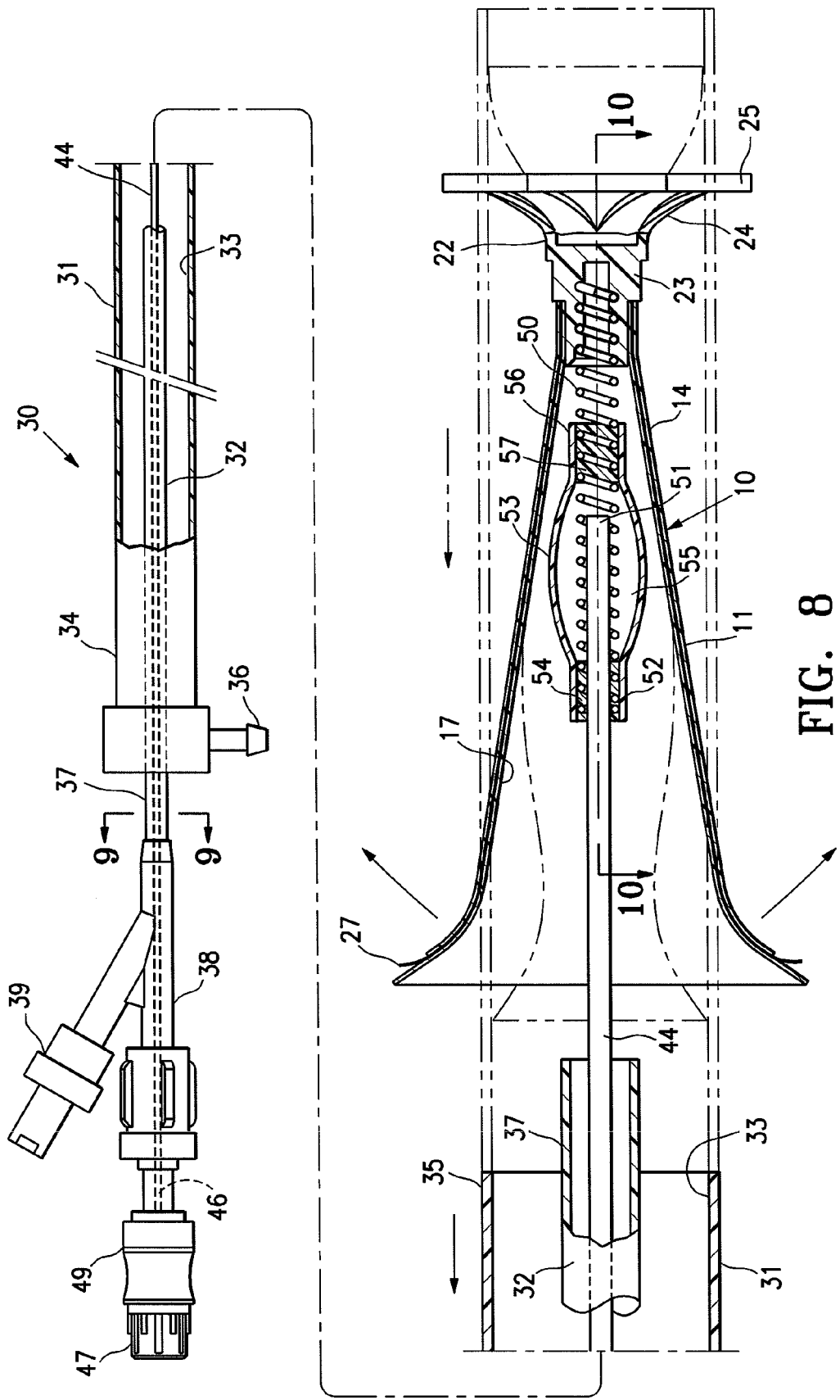
FIG. 8 is a schematic elevational view, partially in section, of a delivery system with the partitioning device shown in FIGS. 1 and 2 mounted thereon.
Figures 9, 10:
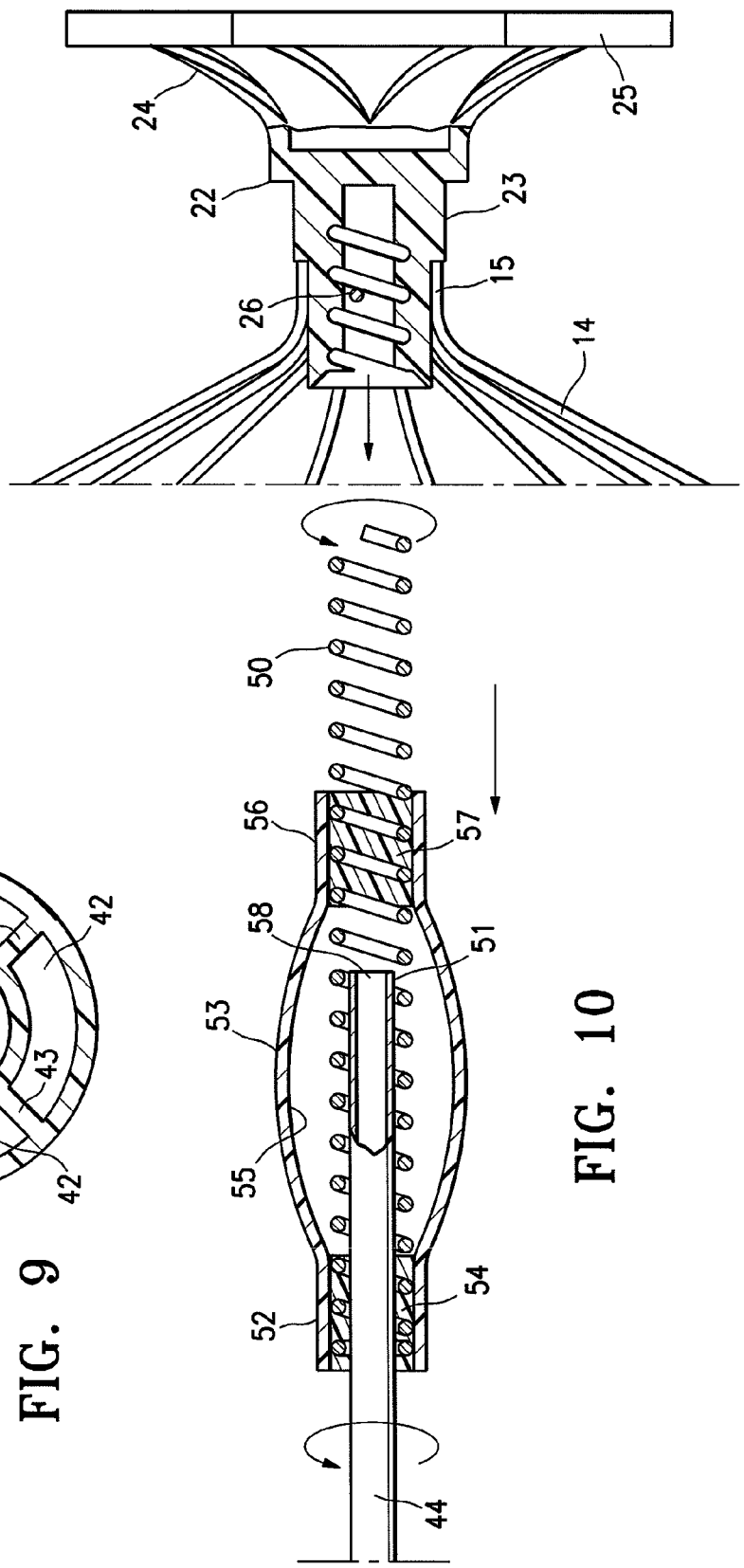
FIG. 9 is a transverse cross-sectional view of the delivery system shown in FIG. 8 taken along the lines 9-9.
FIG. 10 is an elevational view, partially in section, of the hub shown in FIG. 5 being secured to the helical coil of the delivery system shown in FIG. 8.

The hub 12 shown in FIGS. 4 and 5 may connect to a non-traumatic support component 22. The support component 22 has a stem 23 a plurality of pods or feet 24 extending radially away from the center line axis and the ends of the feet 24 are secured to struts 25 which extend between adjacent feet. A plane of material (not shown) may extend between adjacent feet 24 in a web-like fashion to provide further support in addition to or in lieu of the struts 25. The inner diameter of the stem 23 is threaded to secure the partitioning device 10 to a delivery catheter as shown in FIGS. 8-10.

Figure 6:
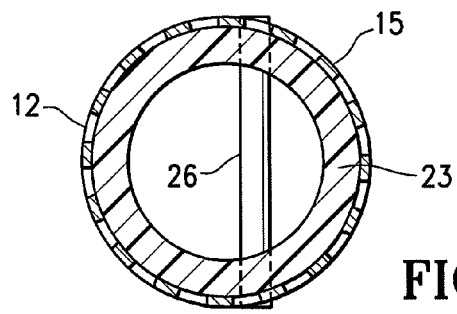
FIG. 6 is a transverse cross sectional view of the hub shown in FIG. 5 taken along the lines 6-6.

In the variation shown in FIG. 5, the distal ends 15 of the ribs 14 are secured within the hub 12 and, as shown in FIG. 6, a transversely disposed connector bar 26 may be secured within the hub which is configured to secure the hub 12 to the atraumatic support component 22.

Figure 2:
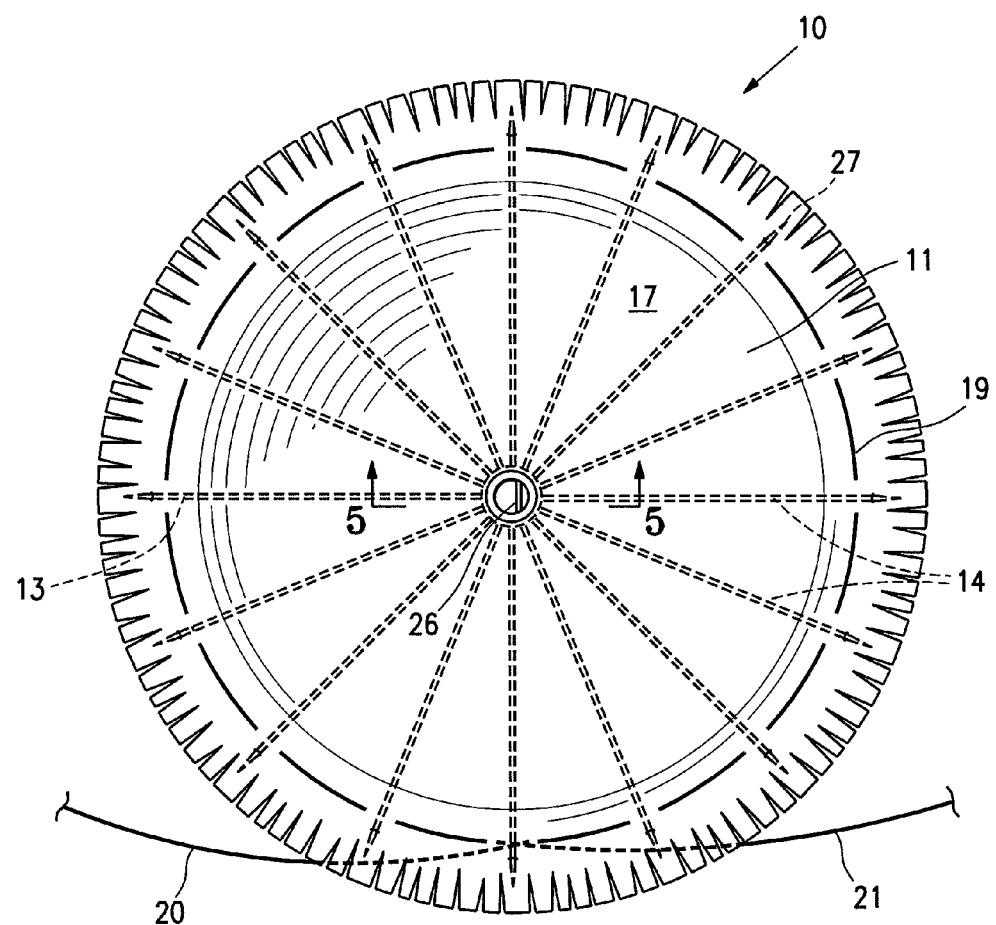
FIG. 2 is a plan view of the partitioning device shown in FIG. 1 illustrating the upper surface of the device.
Figure 3:
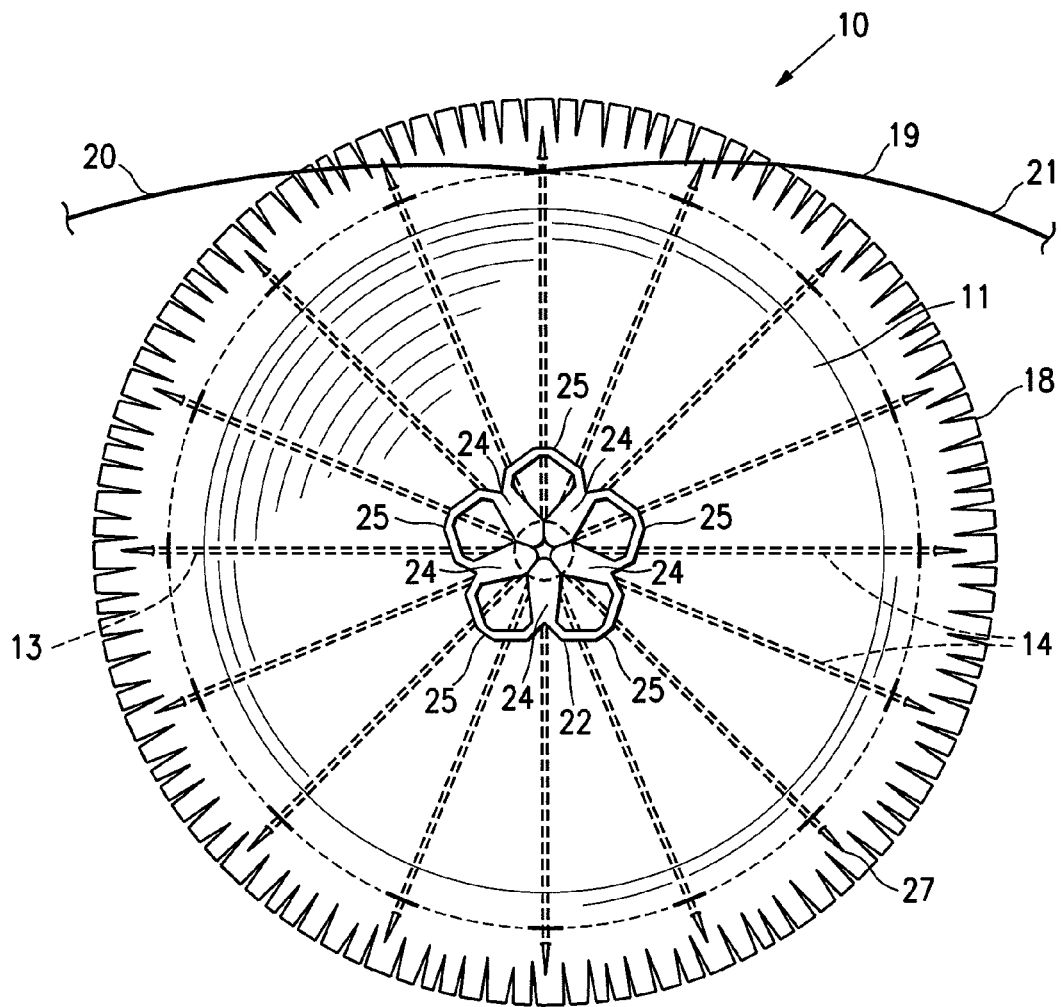
FIG. 3 is bottom view of the partitioning device shown in FIG. 1.

As illustrated in FIGS. 5 and 6, the connector bar 26 of the hub 12 allows the partitioning device 10 to be secured to the non-traumatic support component 22 and to be released from the delivery system within the patient's heart chamber. The distal ends 15 of the reinforcing ribs 14 are secured within the hub 12 in a suitable manner or they may be secured to the surface defining the inner lumen or they may be disposed within channels or bores in the wall of the hub 12. The distal end of the ribs 14 are pre-shaped so that when the ribs are not constrained, other than by the membrane 11 secured thereto (as shown in FIGS. 1 and 2), the free proximal ends 16 thereof expand to a desired angular displacement away from the centerline axis which is about 20° to about 90°, preferably about 50° to about 80°. The unconstrained diameter of the partitioning device 10 may be greater than the diameter of the heart chamber at the deployed location of the partitioning device so that an outward force is applied to the wall of the heart chamber by the partially expanded ribs 14 during systole and diastole so that the resilient frame 13 augments the heart wall movement.

Figure 7:
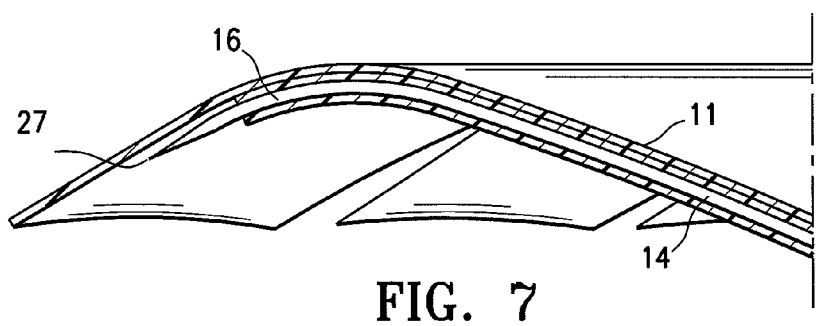
FIG. 7 is a longitudinal view, partially in section of a reinforcing rib and membrane at the periphery of the partitioning device shown in FIG. 1.

FIG. 7 illustrates the curved free proximal ends 16 of ribs 14 which are provided with sharp tip elements 27 configured to engage and preferably penetrate into the wall of the heart chamber and hold the partitioning device 10 in a deployed position within the patient's heart chamber so as to partition the ventricular chamber into a productive portion and a non-productive portion.

FIGS. 8-10 illustrate one variations of a delivery system 30 for delivering a partitioning device 10 such as the one shown in FIGS. 1 and 2 into a patient's heart chamber and deploying the partitioning device to partition the heart chamber as shown in FIGS. 11A-11E. This example of a delivery system 30 includes a guide catheter 31 and a delivery catheter 32.

The guide catheter 31 has an inner lumen 33 extending between the proximal end 34 and distal end 35. A hemostatic valve (not shown) may be provided at the proximal end 34 of the guide catheter 31 to seal about the outer shaft 37 of the delivery catheter 32. In this example, the guide catheter includes a flush port 36 on the proximal end 34 of guide catheter 31 that is in fluid communication with the inner lumen 33.

The delivery catheter 32 has an outer shaft 37 with an adapter 38 on the proximal end thereof having a proximal injection port 39 which is in fluid communication with the interior of the shaft 37. As shown in more detail in FIG. 9, the outer shaft 37 has an inner shaft 41 which is disposed within the interior thereof and is secured to the inner surface of the outer shaft 37 by webs 43 which extend along a substantial length of the inner shaft. The injection port 39 is in fluid communication with the passageways 42 between the inner and outer shafts 41 and 37 respectively and defined in part by the webs 42. A torque shaft 44, which is preferably formed of hypotubing (e.g. formed of stainless steel or superelastic NiTi), is disposed within the inner lumen 45 of the inner shaft 41 and has a proximal end 46 secured within the adapter 38. Balloon inflation port 47 is in fluid communication with the inner lumen 48 of the torque shaft 44. In some variations, additional passageways may be present in the delivery catheter. For example, a filling passageway may be included that may be used to fill the non-productive region behind the partitioning device with one or more fillers (e.g., coils, fluids, etc.). In some variations, an additional inflation lumen may be included for inflating a sealing element (e.g., a sealing balloon).

Torque shaft 44 may be rotatably disposed within the inner lumen 45 of the inner shaft 41 and secured to rotating knob 49. A helical coil screw 50 may be secured to the distal end 51 of the torque shaft 44 and rotation of the torque knob 49 on the proximal end 46 of the torque shaft 44 rotates the screw 51 to facilitate deployment of a partitioning device 10. The proximal end 52 of inflatable balloon 53 may be sealingly secured by adhesive 54 about the torque shaft 44 proximal to the distal end 51 of the torque shaft. The balloon 53 may have an interior 55 in fluid communication with the inner lumen 48 of the torque shaft 44. Inflation fluid may be delivered to the balloon interior 55 through port 47 which is in fluid communication with the inner lumen 48 of the torque shaft 44. The distal end 56 of the balloon 53 in this example is sealingly secured by adhesive 57 to the helical screw 50. The proximal and distal ends 52 and 56 of the balloon 53 are blocked by the adhesive masses 54 and 57 to prevent the loss of inflation fluid delivered to the interior 55 of the balloon 53. Delivery of inflation fluid through a fluid discharge port 58 in the distal end 51 of the torque shaft 44 inflates the balloon 53 which in turn applies pressure to the proximal surface of the partitioning device 10 to facilitate securing the partitioning component 10 to the wall 59 of heart chamber 60 as shown in FIGS. 11A-11E discussed below.

Figure 11A:
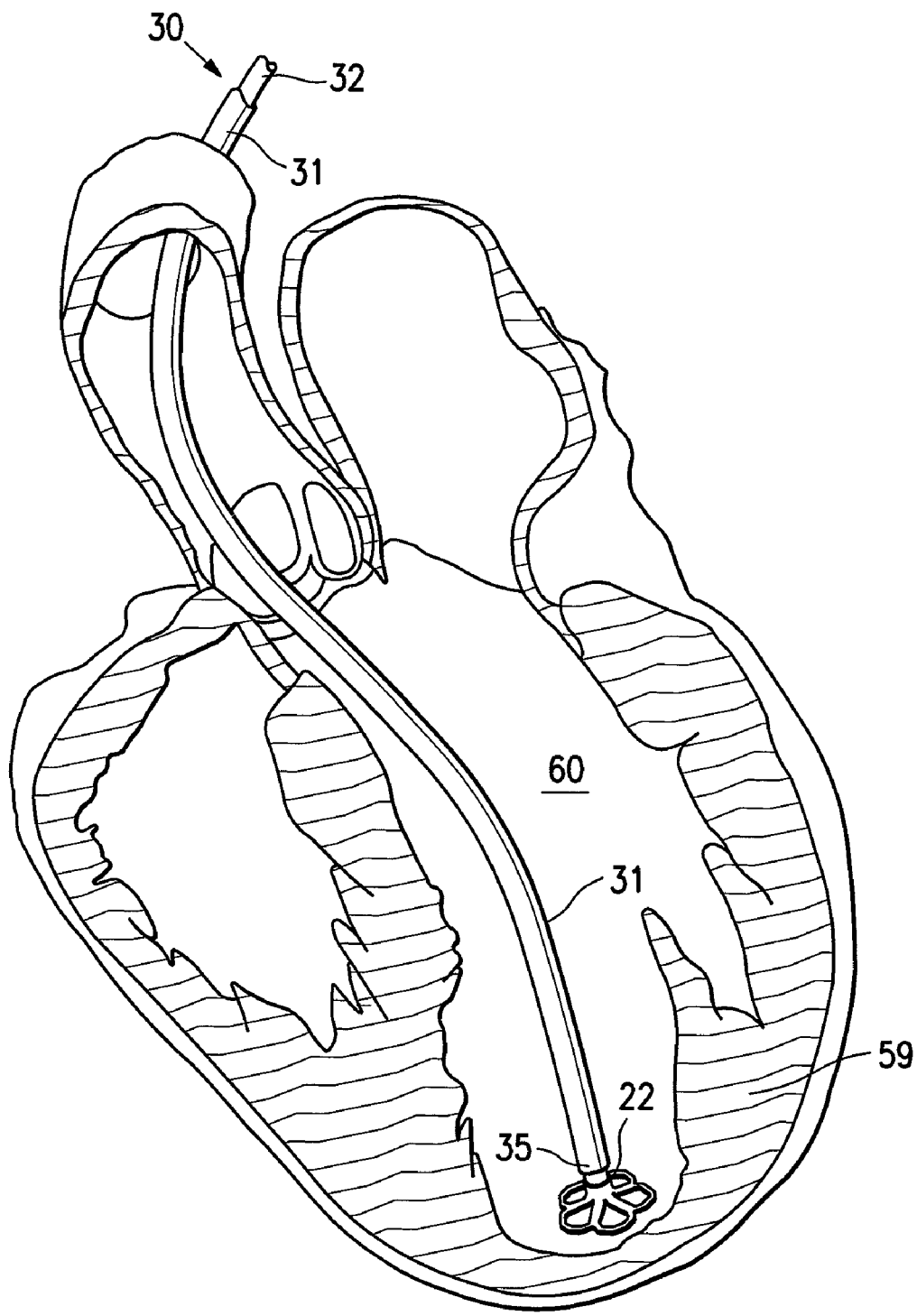
FIGS. 11A-11E are schematic views of a patient's left ventricular chamber illustrating the deployment of the partitioning device shown in FIGS. 1 and 2 with the delivery system shown in FIG. 8 to partition a patient's heart chamber (left ventricle) into a primary productive portion and a secondary, non-productive portion.

In the example shown in FIG. 11A, the partitioning component 10 is delivered through a delivery system 30 which includes a guide catheter 31 and a delivery catheter 32. The partitioning component 10 is collapsed in a first, delivery configuration which has small enough transverse dimensions to be slidably advanced through the inner lumen 33 of the guide catheter 31. Preferably, the guide catheter 31 has been previously percutaneously introduced and advanced through the patient's vasculature, such as the femoral artery, in a conventional manner to the desired heart chamber 60. The delivery catheter 32 with the partitioning component 10 attached is advanced through the inner lumen 33 of the guide catheter 31 until the partitioning component 10 is ready for deployment from the distal end of the guide catheter 31 into the patient's heart chamber 60 to be partitioned.

Figure 11B:
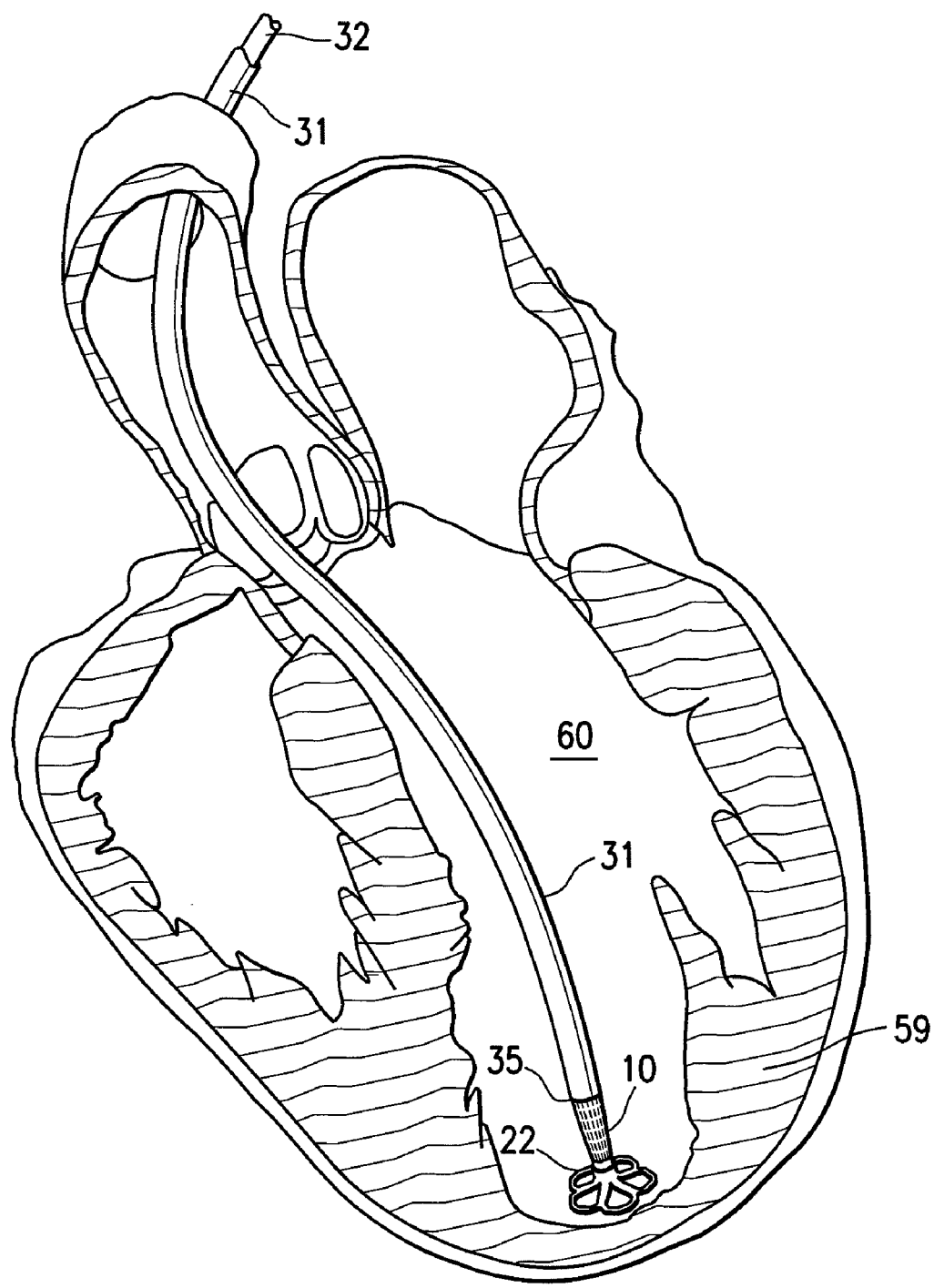
Figure 11C:
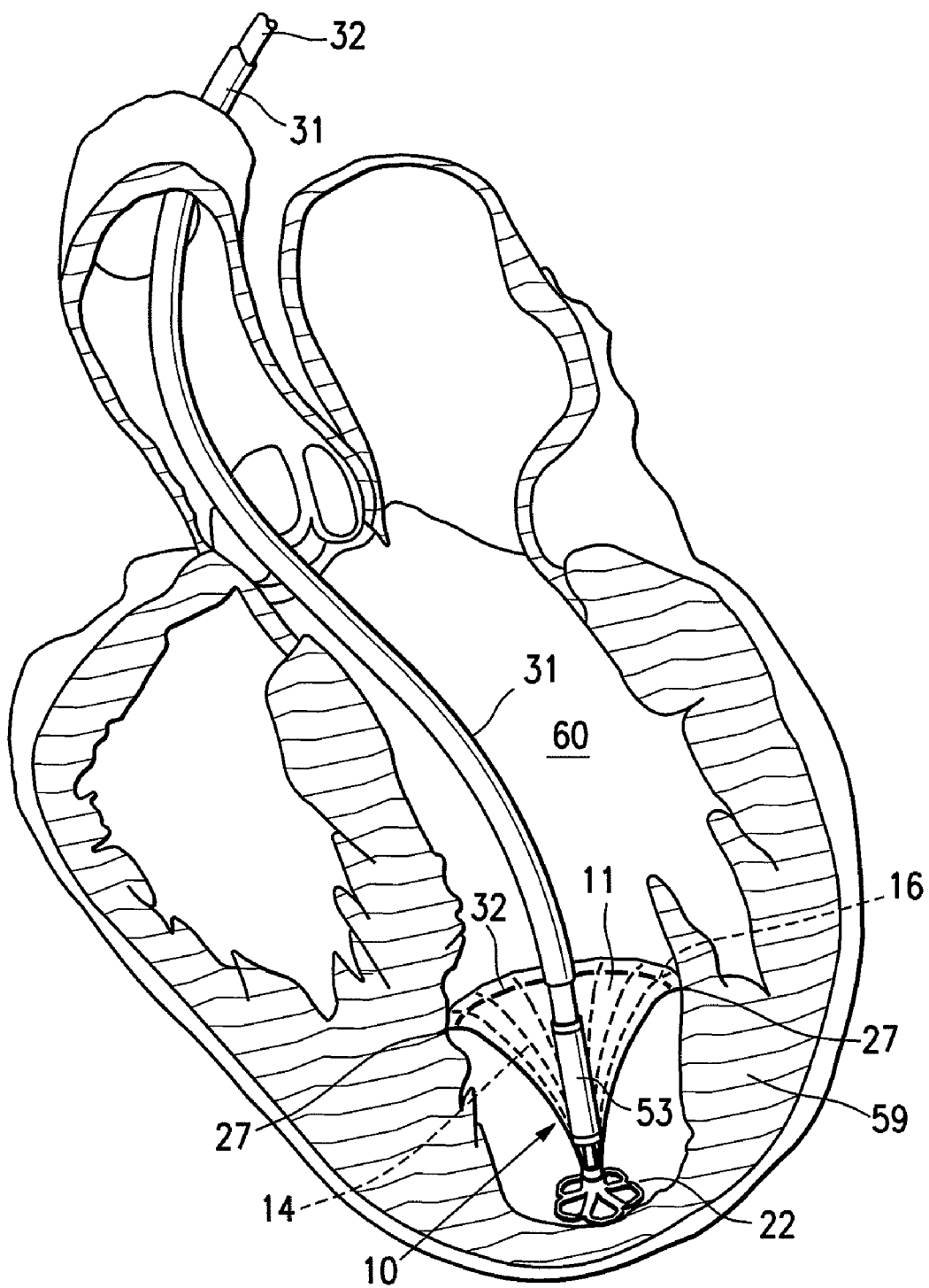

As shown in FIG. 11B, the partitioning component 10 mounted on the screw 50 is urged further out of the inner lumen 33 of the guide catheter 32 until the support component 22 engages the heart wall 59. The guide catheter 31 is withdrawn while the delivery catheter 32 is held in place until the proximal ends 16 of the ribs 14 exit the distal end 35 of the guide catheter. As shown in FIG. 11C, the free proximal ends 16 of ribs 14 expand outwardly to press the sharp proximal tips 27 of the ribs 14 against and preferably into the tissue lining the heart wall 59.

Figure 11D:
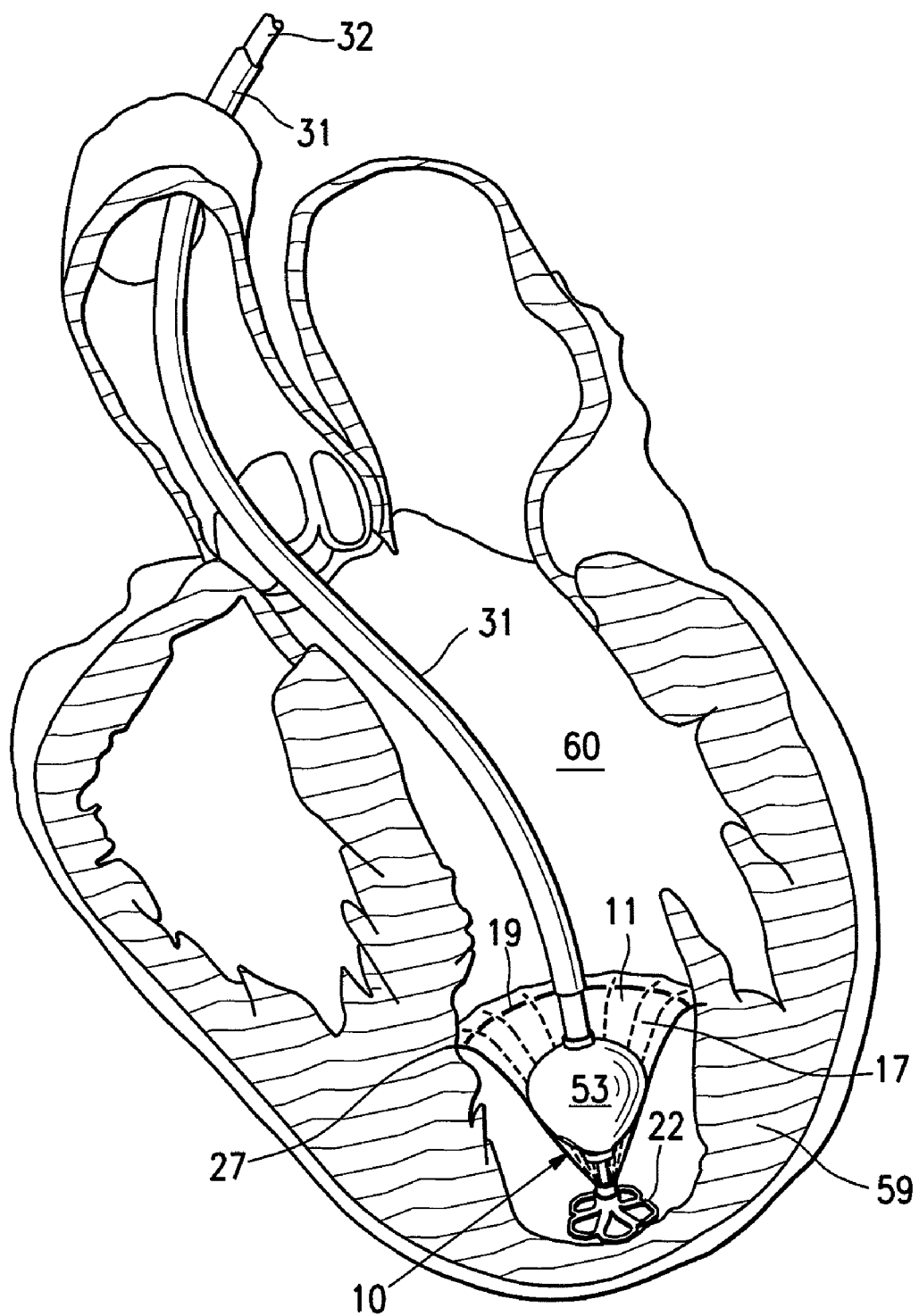

With the partitioning component 10 deployed within the heart chamber 60 and preferably partially secured therein, inflation fluid is introduced through the inflation port 58 in the distal end 51 torque shaft 44 where it is directed into the balloon interior 54 to inflate the balloon 53. The inflated balloon 53 presses against the pressure receiving surface 17 of the membrane 11 of the partitioning component 10 to ensure that the sharp proximal tips 27 are pressed well into the tissue lining the heart wall 59 as shown in FIG. 11D.

In some variations, the partitioning device may include one or more inflatable elements that may be used to expand the device (or assist with expansion), as describe in greater detail below in reference to FIGS. 30A-30D. Thus the applicator (e.g., guide and/or delivery catheters) may not include an inflatable balloon 53. Instead, the applicator may include a connector to connect to the inflatable elements on (e.g., the periphery of) the partitioning device.

With the partitioning device 10 properly positioned within the heart chamber 60, the knob 49 on the torque shaft 44 (as shown in FIG. 8) is rotated counter-clockwise to disengage the helical coil screw 50 of the delivery catheter 32 from the stem 23 secured within hub 12. The counter-clockwise rotation of the torque shaft 44 rotates the helical coil screw 50 which rides on the connector bar 26 secured within the hub 12. Once the helical coil screw 50 disengages the connector bar 26, the delivery system 30, including the guide catheter 31 and the delivery catheter 32, may then be removed from the patient.

The proximal end 34 of the guide catheter 31 in this example is provided with a flush port 36 to inject fluids such as therapeutic, diagnostic or other fluids through the inner lumen 33 during the procedure. Similarly, the proximal injection port 39 of adapter 38 is in communication with passageways 43 if the delivery catheter 32 for essentially the same purpose.

Figure 11E:
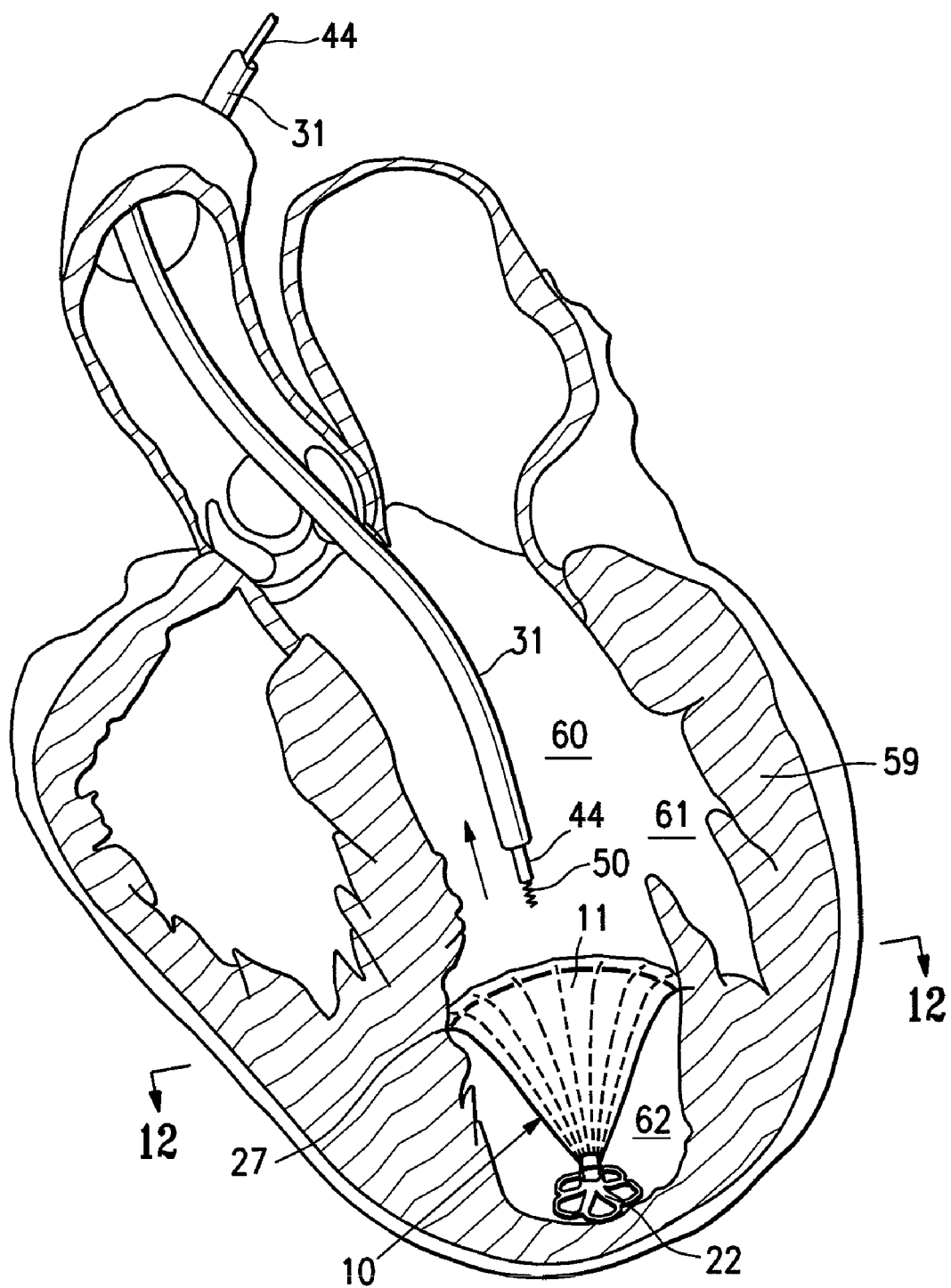

The deployment of the partitioning component 10 in the patient's heart chamber 60 as shown in FIG. 11E divides the chamber into a main productive or operational portion 61 and a secondary, essentially non-productive portion 62. The operational portion 61 is smaller than the original heart chamber 60 and provides for an improved ejection fraction and an improvement in blood flow. Over time, the non-productive portion 62 may fill first with thrombus and subsequently with cellular growth. Bio-resorbable fillers such as polylactic acid, polyglycolic acid, polycaprolactone and copolymers and blends may be employed to initially fill the non-productive portion 62. Fillers may be suitably supplied in a suitable solvent such as dimethylsulfoxide (DMSO). Other materials which accelerate tissue growth or thrombus may be deployed in the non-productive portion 62 as well as non-reactive fillers. Fillers may include solid materials or liquid materials, or both, and may include material that expands after being loaded into the non-productive portion or a chamber within the non-productive portion. For example, the filler may be a coil such as a vasoocclusive coil.

As described in greater detail below, the partitioning devices described herein may also be sealed against the wall(s) of the heart, so that the material used to fill does not leak (or does not substantially leak. In some variations a chamber (e.g., bag) may also be part of the partitioning device and may be positioned within the non-productive portion and be filled by the filler.

Figure 12:
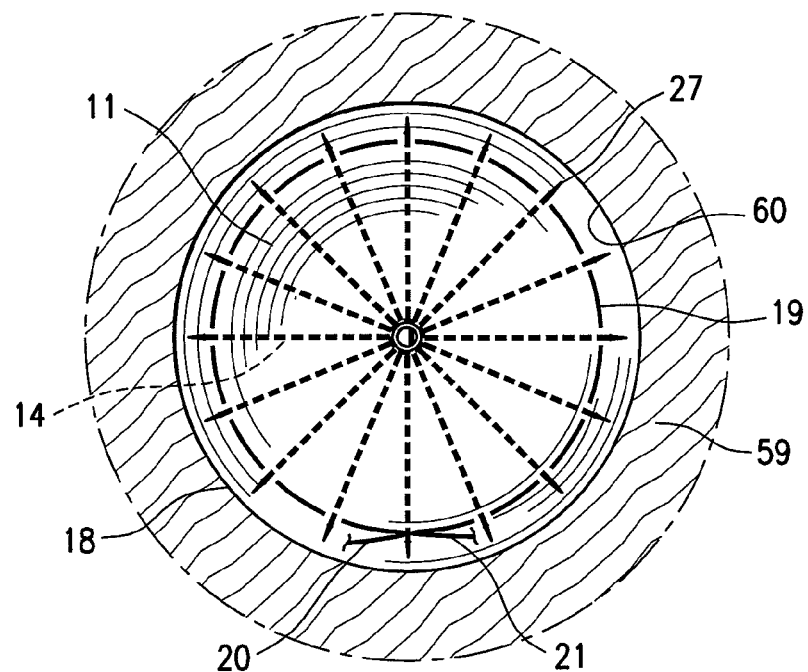
FIG. 12 is a schematic plan view of the deployed device shown in FIG. 11E within a patient's heart chamber.
Figure 13:
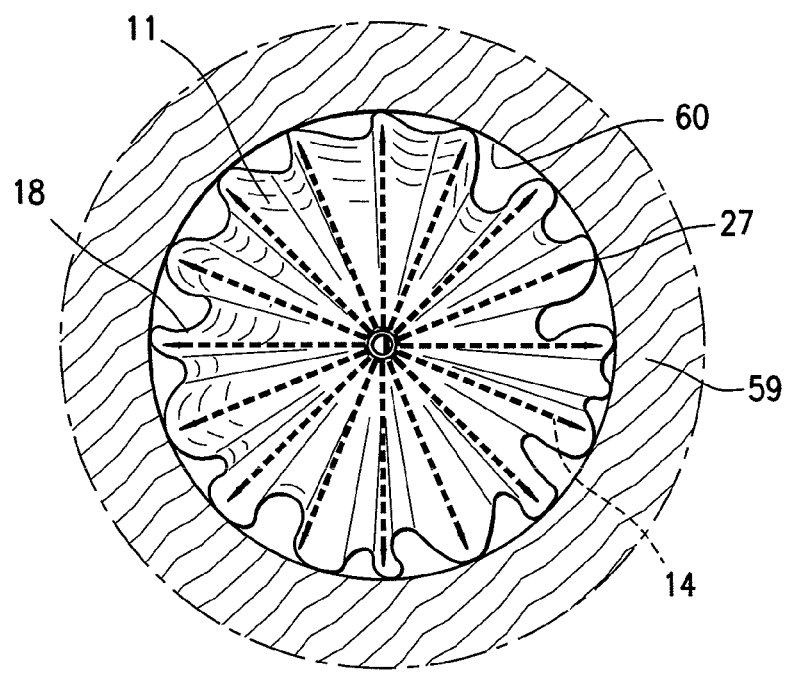
FIG. 13 is a schematic plan view of the partitioning device shown in FIG. 1 without the expansive strand after deployment within a patient's heart chamber.

FIG. 12 is a top view of the deployed partitioning device shown in FIG. 11E schematically illustrating the sealed periphery of the membrane 11 against the ventricular wall. This is to be compared with the schematic presentation shown in FIG. 13 which illustrates a partitioning device without a sealing element such as a strand (or other expandable sealing element) having folds along the periphery 18 which do not allow for an effective seal against the wall 59 of the heart chamber 60. The partitioning device 10 may be conveniently formed by the method described in co-pending application Ser. No. 10/913,608, filed on Aug. 5, 2004, which is incorporated herein by reference.

While porous ePTFE material is preferred, the membrane 11 may be formed of suitable biocompatible polymeric material which includes Nylon, PET (polyethylene terephthalate) and polyesters such as Hytrel. The membrane 11 may be foraminous in nature to facilitate tissue ingrowth after deployment within the patient's heart. The delivery catheter 32 and the guiding catheter 31 may be formed of suitable high strength polymeric material such as PEEK (polyetheretherketone), polycarbonate, PET, Nylon, and the like. Braided composite shafts may also be employed.

FIGS. 14-16 illustrate the collapse and retrieval of a partitioning device 10 by pulling on the ends 20 and 21 of the expansive strand 19 which extends around the periphery of the membrane 11. Typically, the partitioning device 10 would still be secured to the delivery catheter 32, but the delivery catheter is not shown to simplify the drawings. In FIG. 14 the partitioning device 10 is shown in a partially collapsed configuration. In FIG. 15 the partially collapsed partitioning device 10 is shown being withdrawn into the flared distal end 63 of retrieval catheter 64. FIG. 16 illustrates the completely collapsed partitioning device 10 pulled further into the retrieval catheter 64. The partitioning device 10 may be withdrawn by pulling the device through the inner lumen 65 of the retrieval catheter 64. Optionally, the partitioning device 10 and retrieval catheter may be withdrawn from the patient together.

To assist in properly locating the device during advancement and placement thereof into a patient's heart chamber, parts, e.g. the distal extremity, of one or more of the ribs 14 and/or the hub 12 may be provided with markers at desirable locations that provide enhanced visualization by eye, by ultrasound, by X-ray, or other imaging or visualization means. Radiopaque markers may be made with, for example, stainless steel, platinum, gold, iridium, tantalum, tungsten, silver, rhodium, nickel, bismuth, other radiopaque metals, alloys and oxides of these metals.

Figure 17:
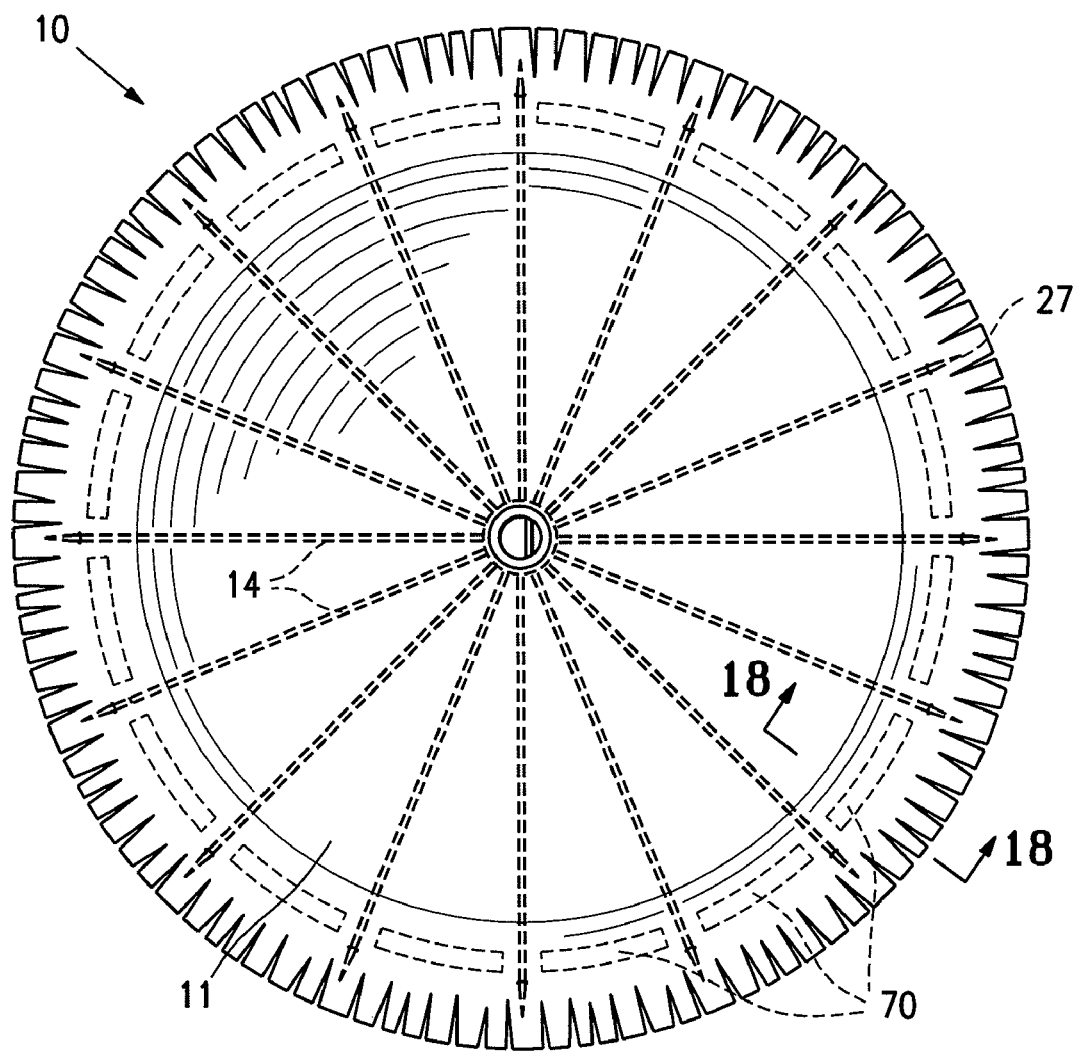
FIG. 17 is a perspective view of the bottom of an alternative partitioning device which has swellable pads disposed between adjacent ribs to press the membrane between the ribs against the heart wall.
Figure 18:
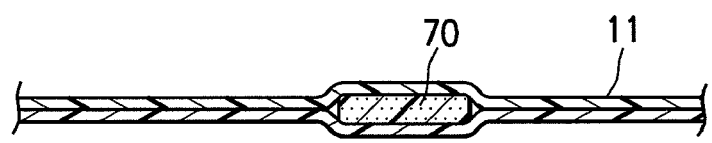
FIG. 18 is a cross-sectional view of a swellable pad disposed between two membrane layers secured to the ribs of the partitioning device.
Figure 19A:
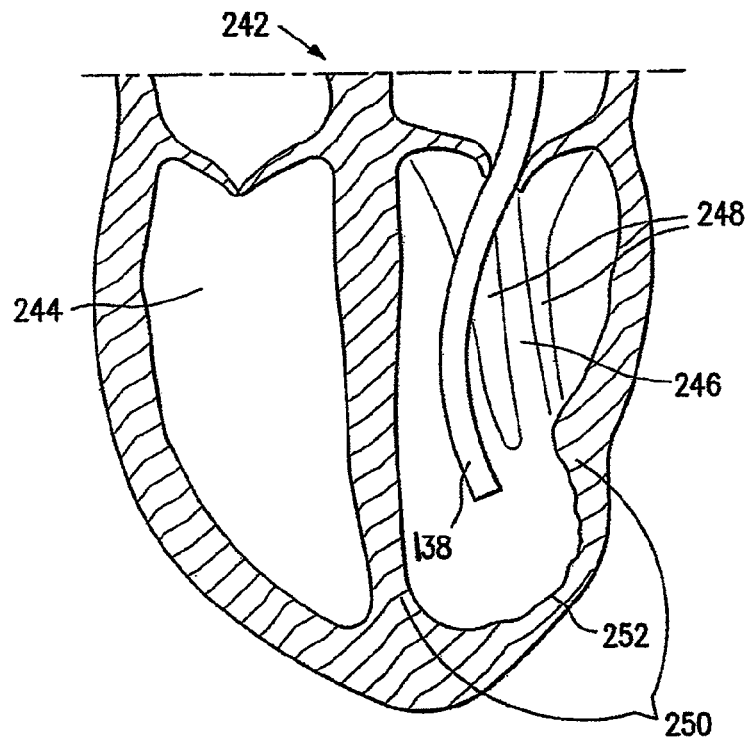
FIG. 19A is a cross-sectional side view of a human heart with the catheter inserted therein.
Figure 19B:
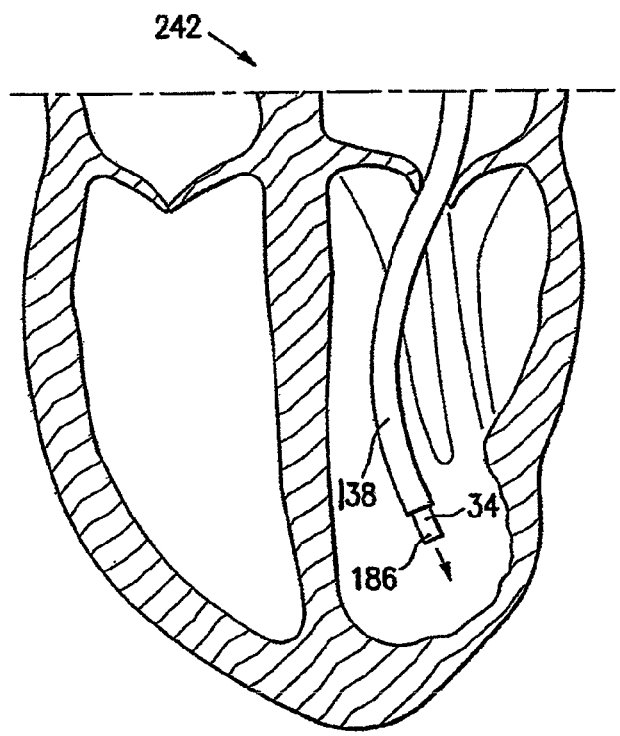
FIGS. 19B-19K are cross-sectional side views of the human heart illustrating installation (FIGS. 19B-19E), removal (FIGS. 19E-19H), and subsequent final installation (FIGS. 191-19K) of the cardiac device.
Figure 19C:
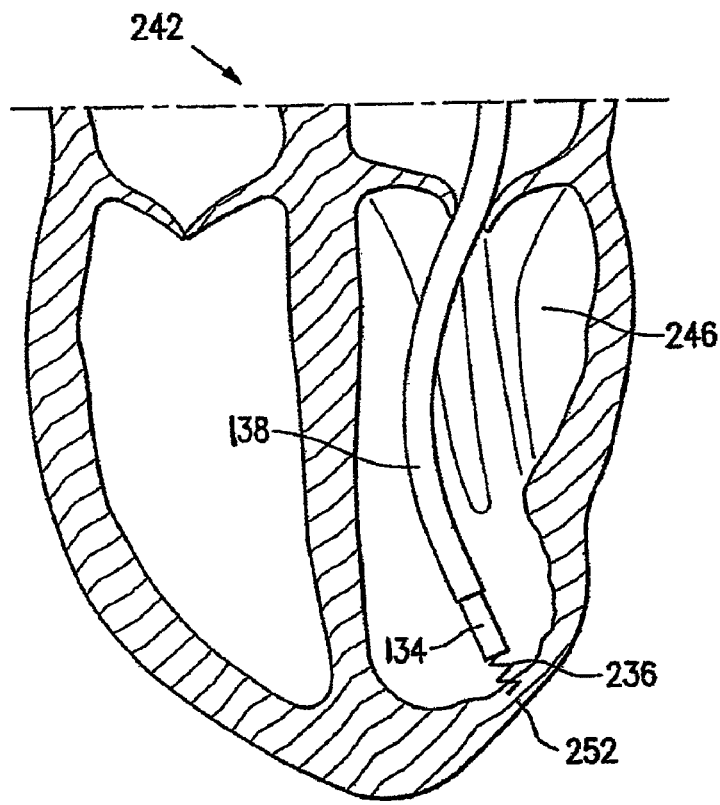
Figure 19D:
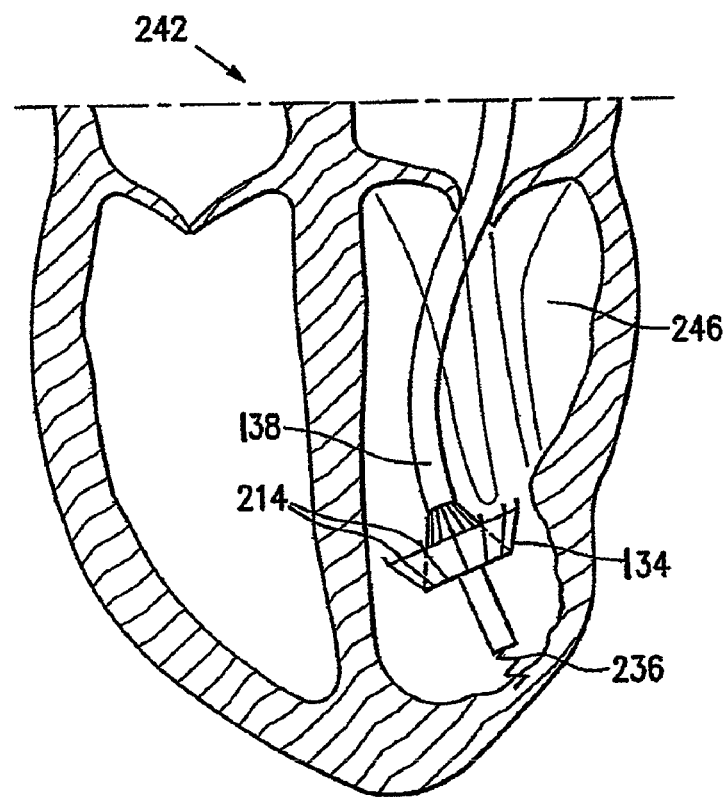
Figure 19E:
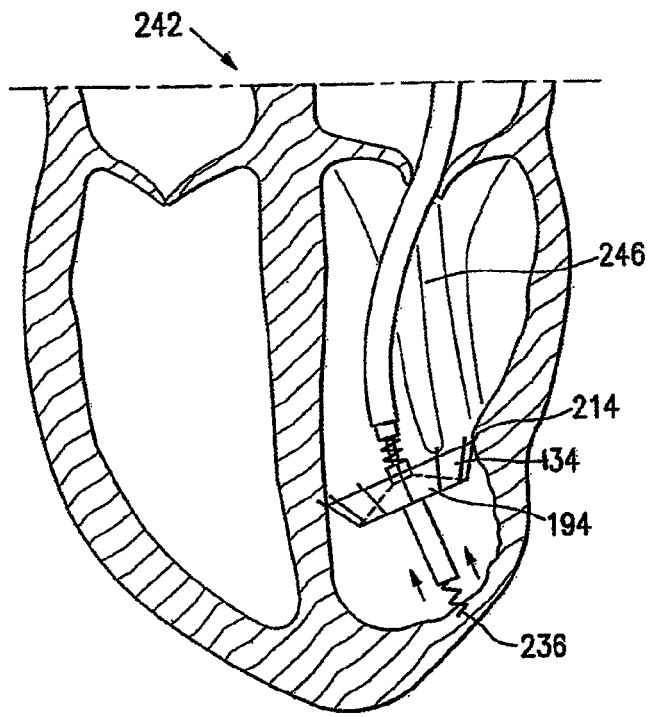
Figure 19F:
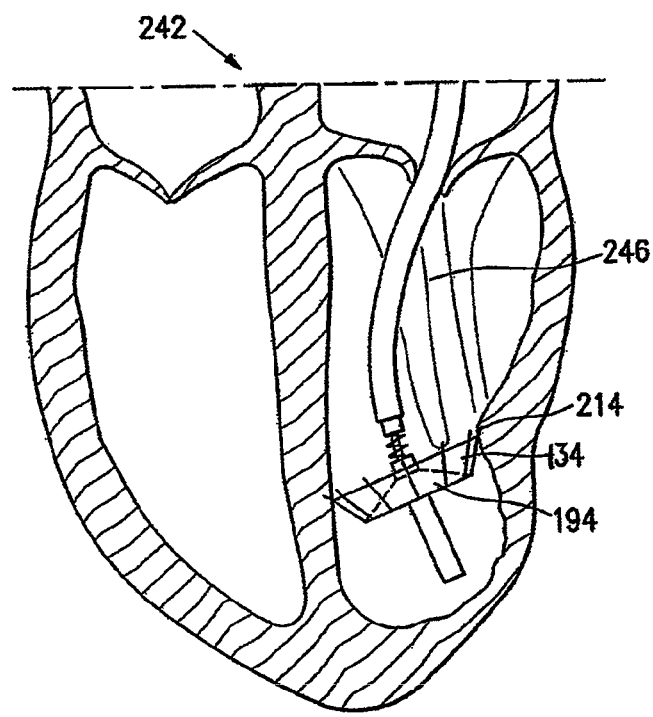
Figure 19G:
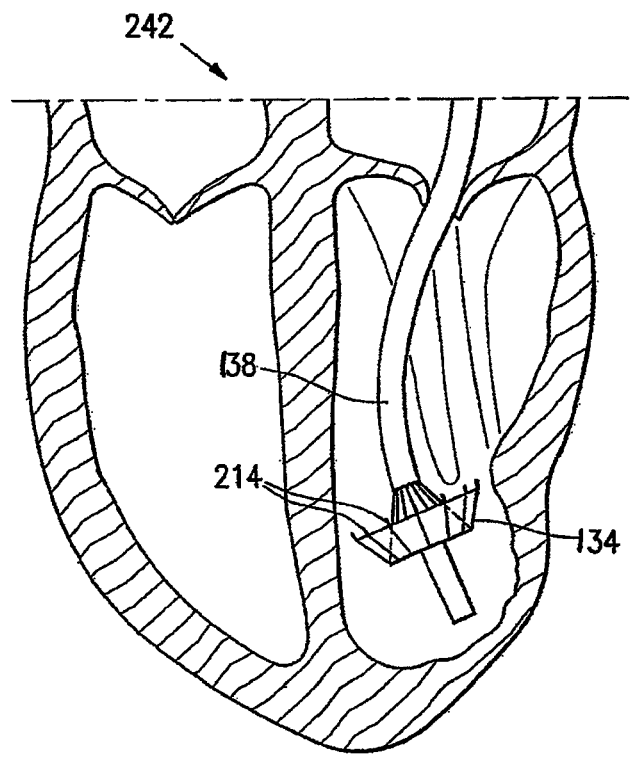
Figure 19H:
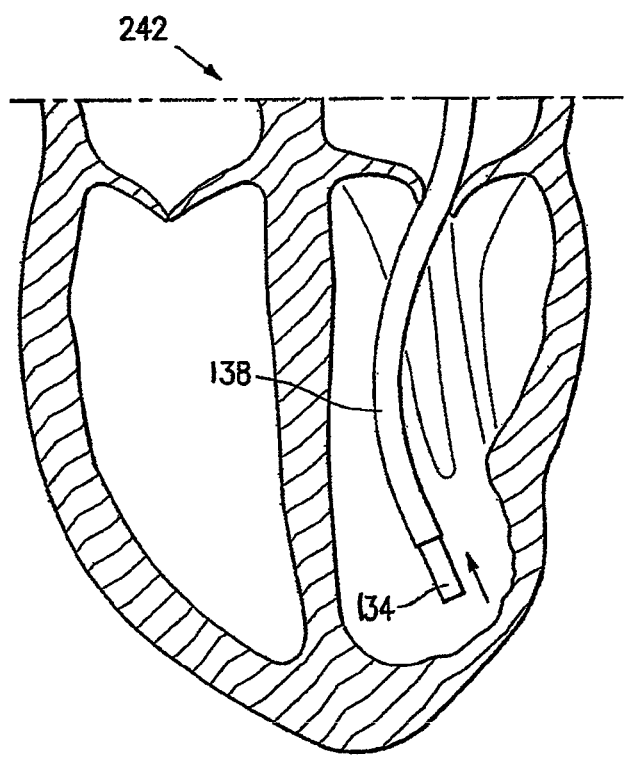
Figure 19I:
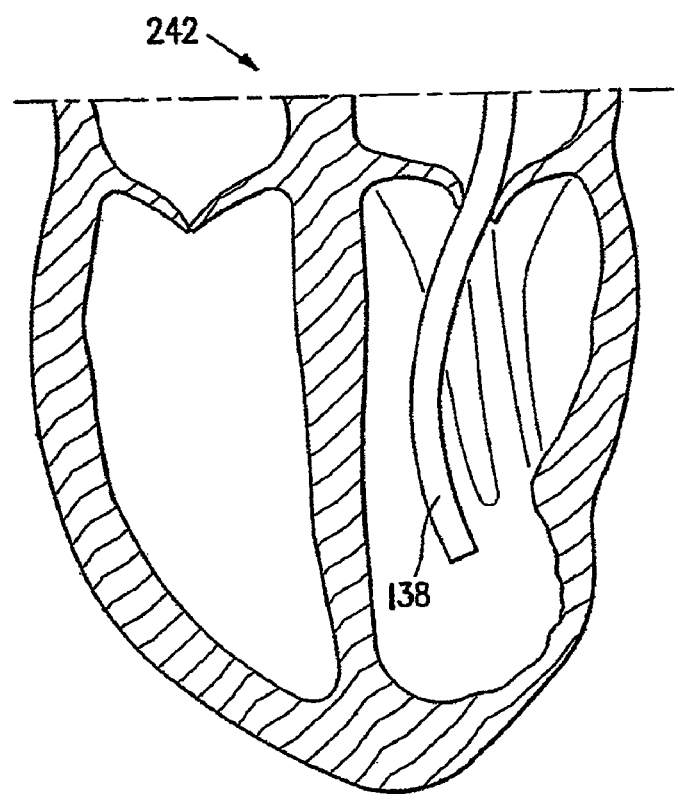
Figure 19J:
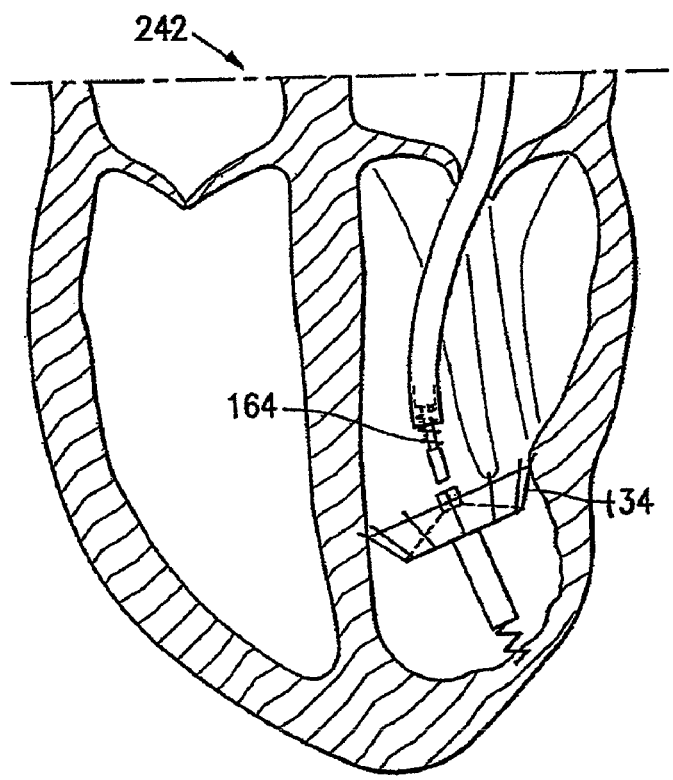
Figure 19K:
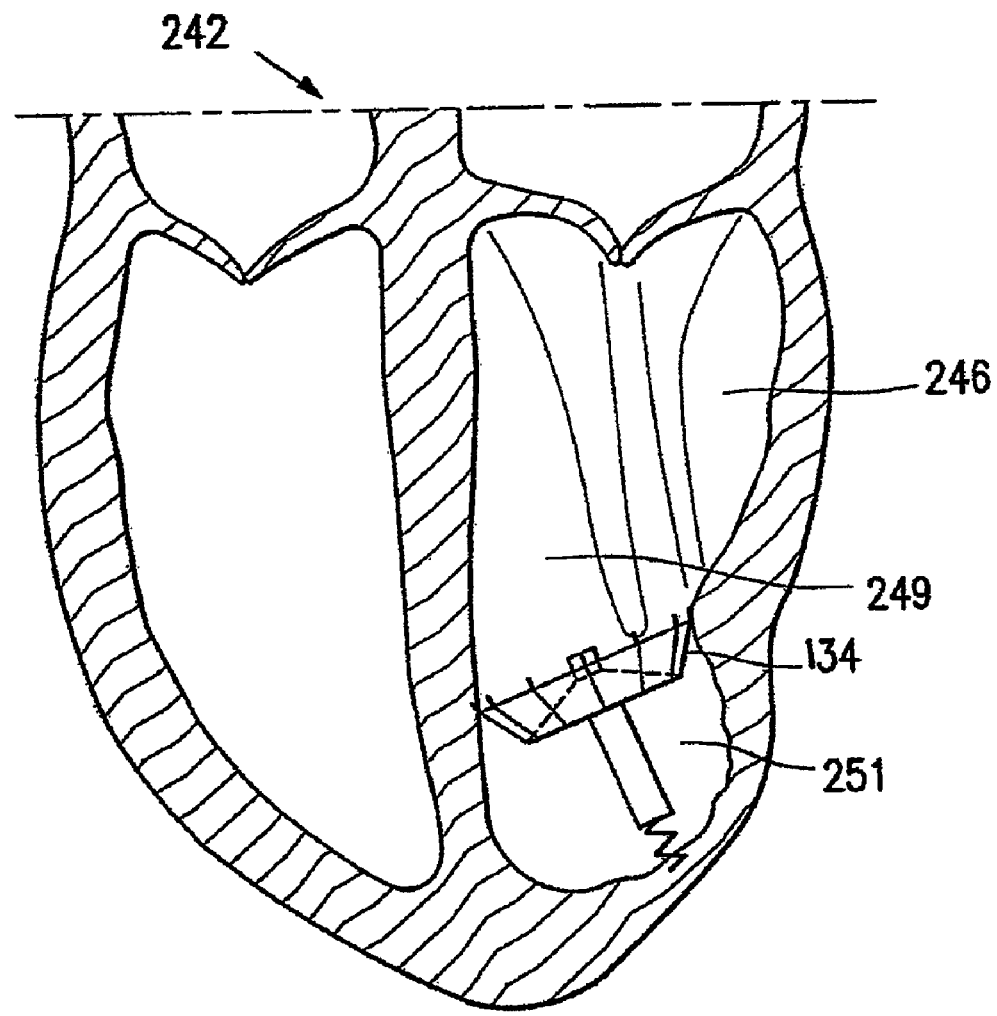

FIGS. 17 and 18 illustrate an alternative design which illustrates a partitioning device 10 that includes an expandable sealing element. In this example, the expandable sealing elements are a plurality of swellable bodies 70, preferably hydrophilic foam, around the periphery of the membrane 11 between adjacent ribs 14. When these bodies contact body fluid, such as blood, upon deployment, they swell, thereby sealing the peripheral portion of the membrane 11 against the patient's heart wall as previously described. The details of the partitioning device 10 may be essentially the same as in the previous embodiment and elements in this alternative embodiment are given the same reference numbers as similar elements in the previous embodiments.

To the extent not otherwise described herein, the various components of the partitioning device and delivery system may be formed of conventional materials and in a conventional manner as will be appreciated by those skilled in the art.

FIGS. 19A-19J illustrate application of another variation of a partitioning device 134 being deployed in a human heart 242. The heart 242 contains a right ventricle 244 and a left ventricle 246 with papillary muscles 248 and an akinetic portion 250 with an apex 252. The distal end of the catheter 138 has been inserted through the aorta and aortic valve into the left ventricle 246 to a selected position where the cardiac device 134 can be deployed. The catheter tube 138 is then partially pulled off of the cardiac device 134 exposing the stem 186.

The active anchor 236 is then deployed by rotating the anchor knob 58 in a first direction. The active anchor 236 penetrates the myocardium of the heart 242 to secure the cardiac device 134 in the selected position at the apex 252 of the akinetic portion 250 of the left ventricle 246. In some variations the device does not include an active (e.g., distal) anchor, but may include an atraumatic foot, as described above.

The catheter 138 is then completely removed from the distal end 54 of the deployment member 46, exposing the cardiac device 134. As the cardiac device 134 expands, due to the resilient nature of the segments 192 and the pre-set shape of the frame 184, the passive anchors 214 on the segments 192 penetrate the myocardium in a first direction. The membrane 194 seals a portion of the ventricle 246 and separates the ventricle 246 into two volumes.

If the cardiac device 134 has not been properly positioned, or if it is of the wrong size or shape for the particular heart, the device 134 may be repositioned or completely removed from the heart 242.

Figure 20A:
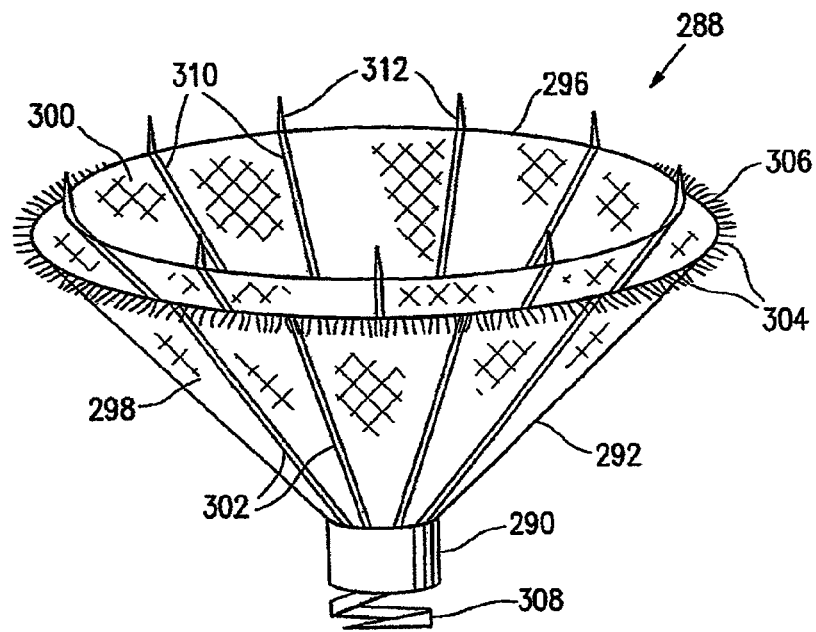
FIG. 20A is a perspective view of a cardiac device according to a further embodiment of the invention.
Figure 20B:
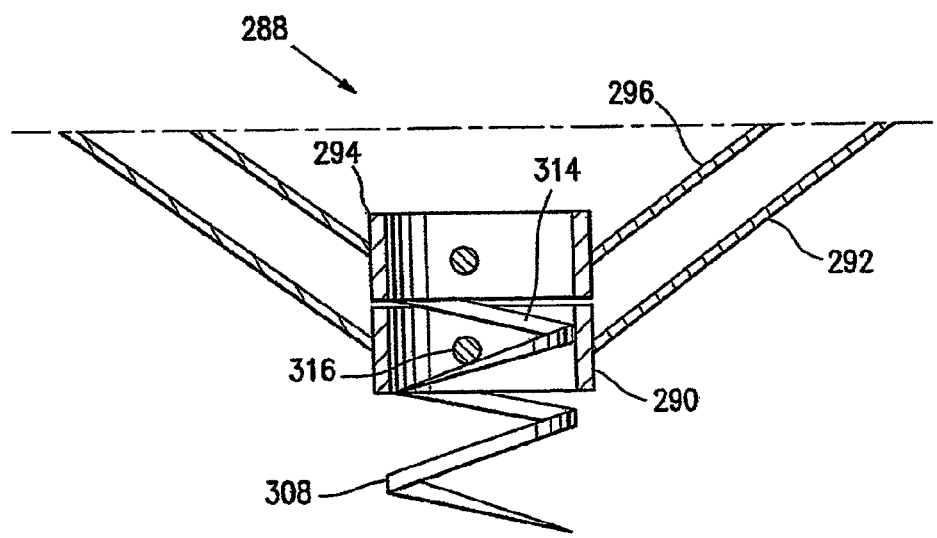
FIG. 20B is a cross-sectional side view of the cardiac device of FIG. 20A.

FIG. 20A and FIG. 20B illustrate another variation of a cardiac (or partitioning) device 288. This example of a partitioning device 288 includes a sealing element that is configured as a second membrane 300 having fibers (or fringe) 304 that acts to seal against the ventricle wall. The partitioning device 288 in FIGS. 20A-20B includes a first hub 290, a first frame 292, a second hub 294, a second frame 296, a first membrane 298, and a second membrane 300. The first hub 290 is attached to a central portion of the first frame 292. A plurality of segments 302 extend radially from and upwards from the first hub 290. The first membrane 298 is occlusive and made of a thrombogenic material and stretched between the segments 302 to form a first cone-shaped body. A plurality of fibers 304 extend radially from an outer edge 306 of the first cone-shaped body. An active anchor 308 extends down from the first hub 290.

The second frame 296 includes a plurality of segments 310 extending radially and upwardly from the second hub 294 and end in sharp passive anchors 312. An attachment screw 314, similar to the detachment screw 214, extends downwards from the second hub 294. Referring specifically to FIG. 20B, the attachment screw 314 is rotated so that it engages a pin 321 within the first hub 290, similarly to the frame hub 190 already described, to secure the second frame 296 to the first frame 292. The second membrane 300 is made of ePTFE and stretched between the segments 310 to form a second cone-shaped body.

Figure 20C:
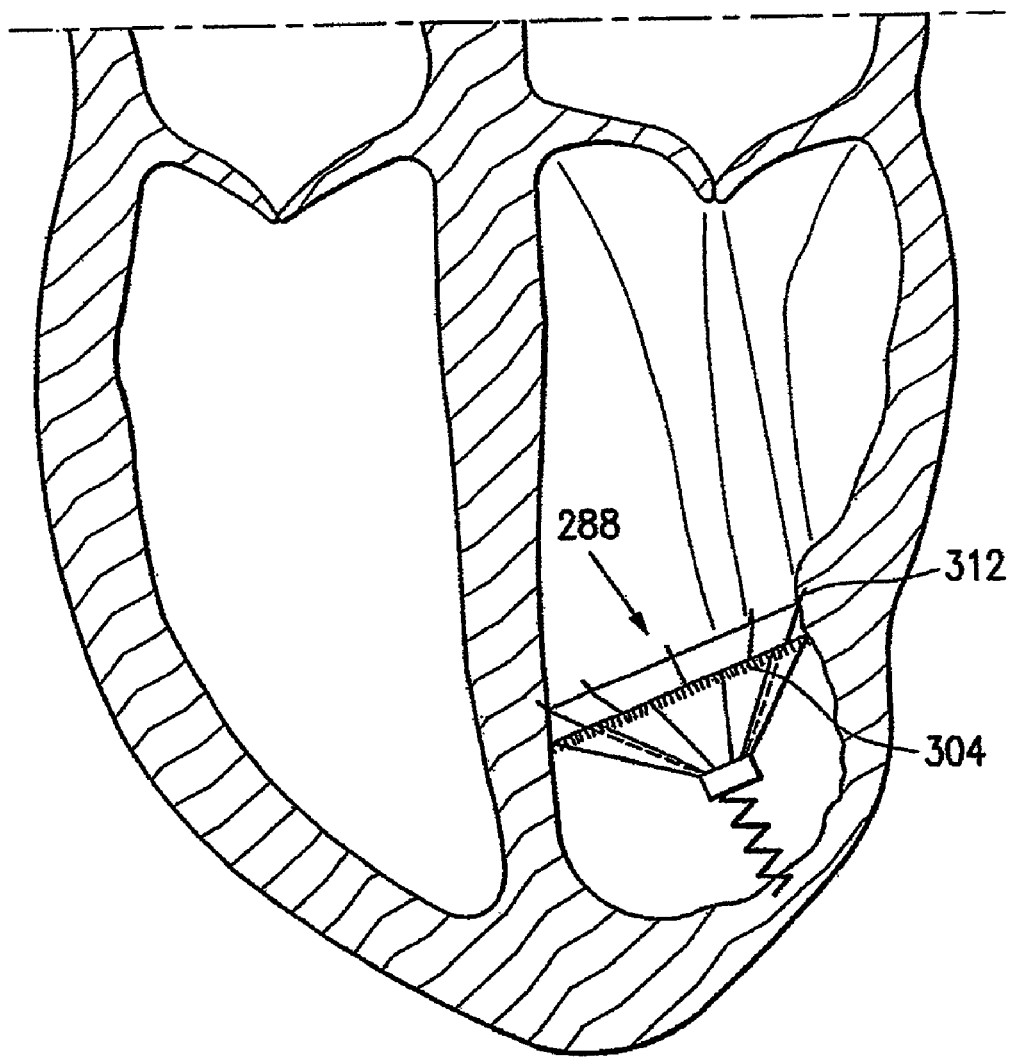
FIG. 20C is a cross-sectional side view of the human heart with the cardiac device of FIG. 20A installed.

FIG. 20C illustrates a human heart with the partitioning device 288 of FIG. 20A secured to an akinetic portion thereof. The fibers 304 on the outer edge 306 of the first frame 292 are interacting with an inner surface of the left ventricle to seal off the volume below the outer edge 306 of the first frame 292. The passive anchors 312 on the ends of the segments 310 of the second frame 296 have penetrated the myocardium to hold the device 288 in place.

A further advantage of this embodiment is that the fibers 304 of the first membrane 298 interface with trabeculae and further block the flow of blood into the apex of the akinetic portion.

In another variation of the partitioning device described herein, the device includes a plurality of strands extending from the distal side of the device. Thus, the sealing element comprises a plurality of strands or braids that extend from the portion of the device within the non-productive side of the device. These braids may press against an inner surface of the ventricle, and help seal the device within the ventricle.

In some variations the sealing element is an inflatable sealing element. For example, the inflatable sealing element may be a swellable element, as described above in FIGS. 17 and 18, which inflates with fluid to swell. Alternatively, the device may include an inflatable sealing element configured as a balloon, as shown in FIGS. 21A-21C.

Figure 21A:
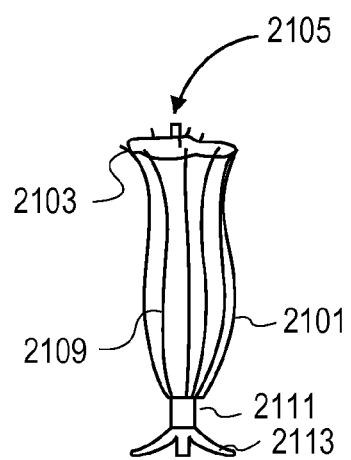
FIGS. 21A-21C illustrate a variation of a partitioning device having an inflatable seal.

FIG. 21A illustrates one variation of a partitioning device in a collapsed or delivery configuration. The device includes a plurality of ribs 2101 to which a membrane 2109 is connected. The ribs connect to a central hub 2111 which connects to an atraumatic foot 2113 in this example. The peripheral region of the membrane includes an inflatable balloon sealing element 2103 having a valve 2015. In FIG. 21A the sealing balloon element 2103 is shown collapsed. The device may be inflated after expanding in the ventricle, or it may be inflated to help expand the device. As mentioned, the delivery catheter may be adapted to communicate with the valve and inflate the device.

Although the valve 2015 for inflation is shown in this example on the periphery of the partitioning device, in some variations, the valve may be located near the center (e.g., radially) of the partitioning device, so that it may be attached to an inflation port on the applicator. In some variations, the partitioning device may include more than one valve.

Figure 21B:
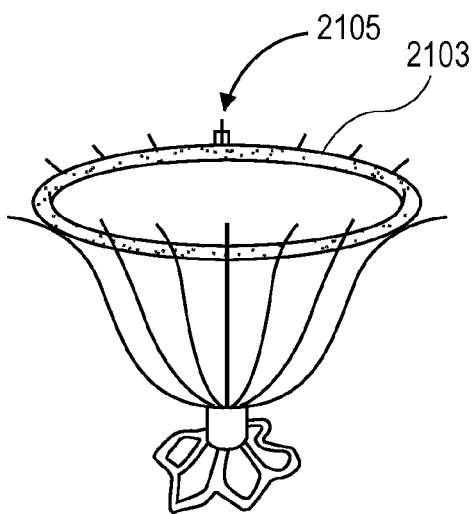
Figure 21C:
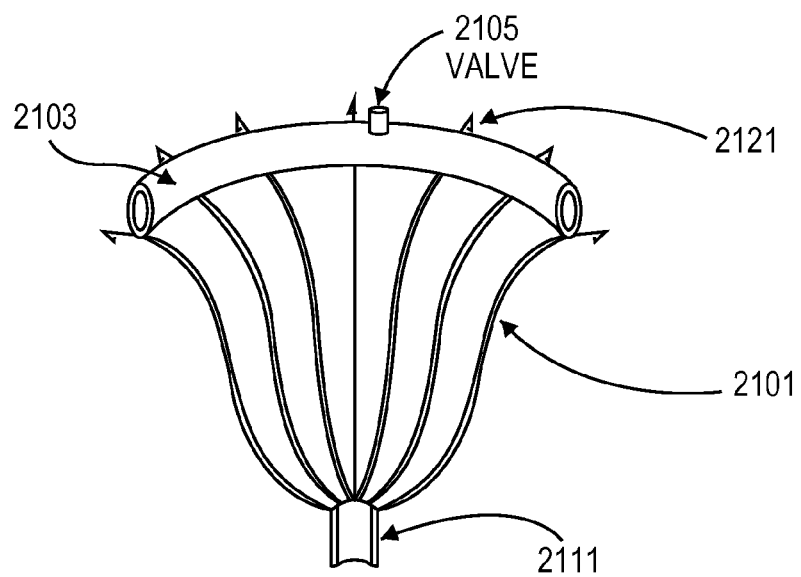

FIG. 21B shows the partitioning device of FIG. 21C in the (at least partially) expanded configuration, in which the balloon around the periphery of the membrane is inflated. As with the swellable variation of the inflatable sealing element, the balloon may be located at the very periphery of the membrane, or it may be positioned more centrally (e.g., towards the centerline of the device), but still configured to apply pressure to urge the membrane against the wall of the heart and thereby seal the membrane to the wall. FIG. 21C shows a partial cut-away version of the inflatable balloon sealing element, including the passive anchors 2111 at the ends of the implant ribs or struts 2101.

Figure 30A:
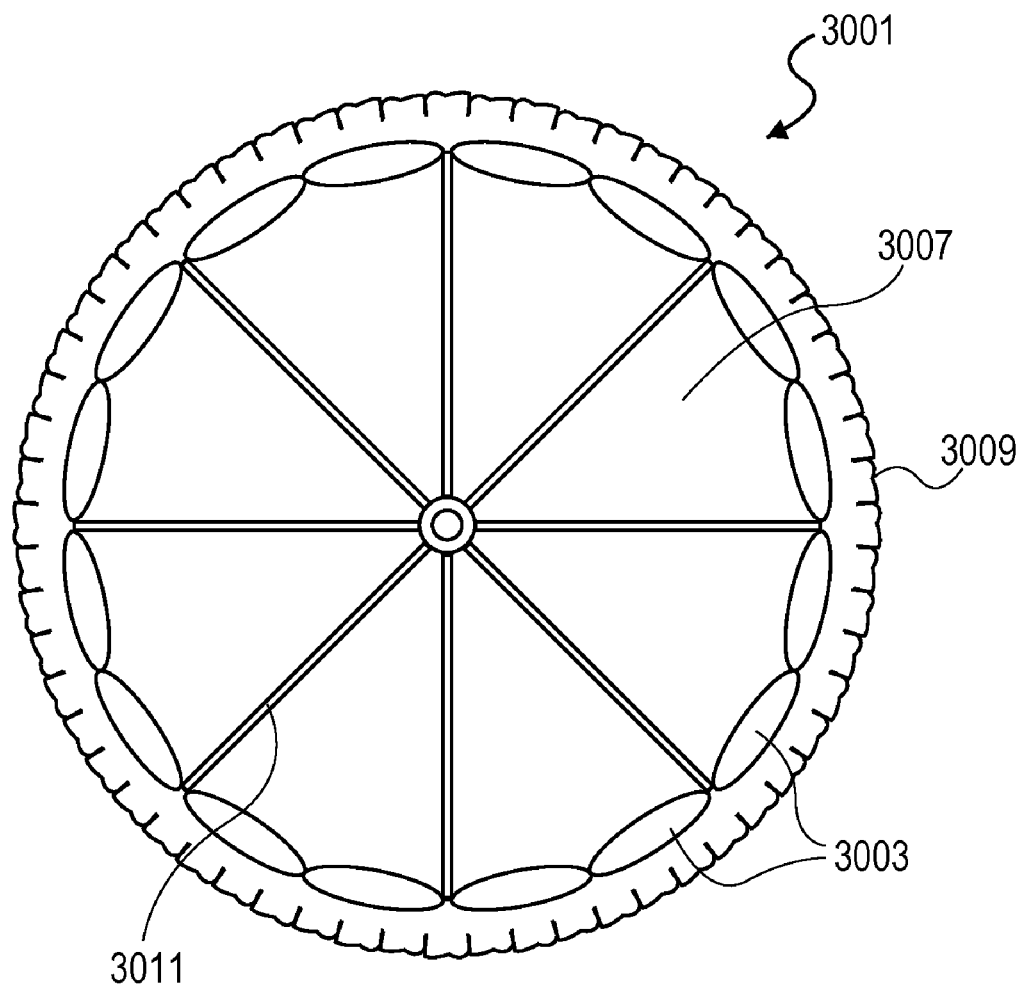
FIGS. 30A and 30B show another variation of a partitioning device including an inflatable sealing element.

FIGS. 30A-30D illustrate another variation of a partitioning device having an inflatable sealing element. In this example, the inflatable sealing element is a plurality of inflatable elements 3003 that are distributed around the perimeter of the device 3001. As mentioned, inflation of these elements may both expand the partitioning membrane into the deployed form, and may also help seal the membrane against the wall of the ventricle. Thus, the expandable element may provide both circumferential and radial expansion of the partitioning device. For example, FIG. 30A shows a top view of the device indicating the partitioning membrane 3007 (having a peripheral region 3009), and the plurality of expandable and inflatable elements 3003. The inflatable elements may be inflated by one or more inflation channels 3011, which may be connected to a port and/or valve that can be connected to the applicator or other source of inflation material (gas, fluid, etc.).

Figure 30B:
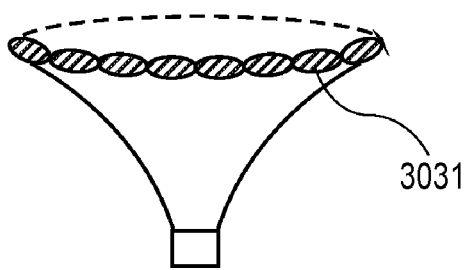

The inflatable balloon or plurality of balloons at or near the periphery of the membrane of the partitioning device may be formed from the same material as the membrane. For example, the balloon may be integral with the membrane by forming cavities between two layers forming the membrane. For example, the membrane may be formed of two layers of ePTFE sandwiched together. In some variations, the struts or arms are laminated between the two layers. As shown in FIG. 30A and 30B, a portion of the membrane may be inflatable by preventing them from sealing (laminating) together.

The inflatable element(s) may be connected via an inflation channel 3011 or a plurality of inflation channels 3011, as shown in FIG. 30A, to a port or valve. As mentioned, the valve may be located in any appropriate location so that it may couple with an inflation source. For example, a valve may be positioned in the hub (center) region that typically mates with the applicator. One or more inflation channels (or inflation ports) may be used. For example, in FIG. 30A, the device includes a plurality of inflation channels distributing inflation material to all of the inflatable balloon elements. When a plurality of inflatable balloon elements are used, the device, each inflatable balloon element may be separately inflatable, or all (or a subset) of the inflatable elements may be connected together so as to inflate together.

As mentioned above, any appropriate inflation material may be used, including liquids (e.g., saline), gases, solids, gels, etc. In some variations, the inflatable element(s) described herein may be filled with a contrast agent that may help visualize the partitioning device. For example, the inflatable elements may be filled with a radioopaque contrast media that allows visualization of the partitioning device after it has been deployed in the left ventricle. In some variations, such as the partitioning device shown in FIG. 30B, the periphery of the membrane may be visualized by inflating with a contrast material 3031.

In some variations, the inflation material is a polymerizable or curable. For example, the inflatable elements (e.g., balloon elements) may be inflated with a curable material including a UV curable material or an RF curable material. For example, the filling material may include a UV-curable filling material. Thus, an applicator may also includes a light-emitting element such as a fiber optic cable and/or a port for an energy source that can apply the energy (light, heat, etc.) to cure or otherwise modify the material in the inflatable element.

In some variations, the partitioning device may include channels or pathways that may be inflated with a curable material to form one or more of the struts. For example, in FIG. 30A, channels 3011 may be formed within the membrane 3007 either for filing the inflatable elements 3003, or simply to form inflatable struts. These inflatable struts may be filled with a curable material, as mentioned above, which may provide additional structural support. For example, when the membrane is formed by lamination or otherwise securing two or more layers, the struts or other inflatable members may be formed between them (e.g., in non-adhesive regions). Alternatively, inflatable regions may be attached to the membrane(s). In some variations, the partitioning device may therefore include one or more inflatable struts that are formed in vivo, for example, using an elastomeric (e.g., RTV-like) curable material. In some variations the inflatable struts extend radially (e.g., from a common hub region), towards to the distal end of the membrane. The inflatable struts may communicate with inflatable members including inflatable balloon members 3003, as shown in FIG. 30A, or they may not communicate with other inflatable regions, but may terminate or include one or more ports.

The inflatable balloon element(s) may be located at or near the peripheral edge of the device. For example, in FIG. 30A, the inflatable balloon elements are located just proximal to the peripheral edge of the device, so that a portion of the membrane extends distally past the inflatable element. This edge portion may be loose, serrated, (or may form a plurality of flaps), and may help seal the device to the wall of the ventricle. In some variations, the inflatable element is at the periphery of the partitioning device.

FIG. 30B illustrates a side view of the partitioning device of FIG. 30A, showing the inflatable balloon elements near the proximal edge of the membrane.

Figure 30D:
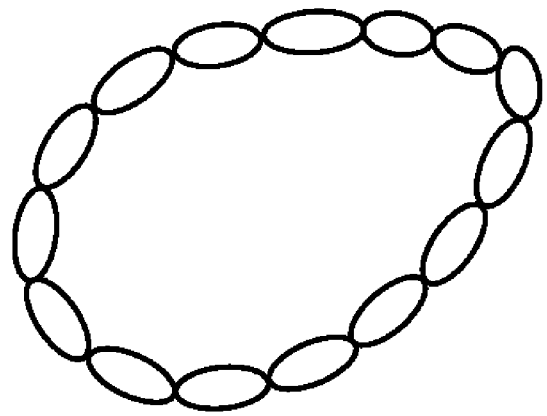
FIG. 30C and 30D illustrate operation of the device shown in FIG. 30A and 30B.
Figure 30C:
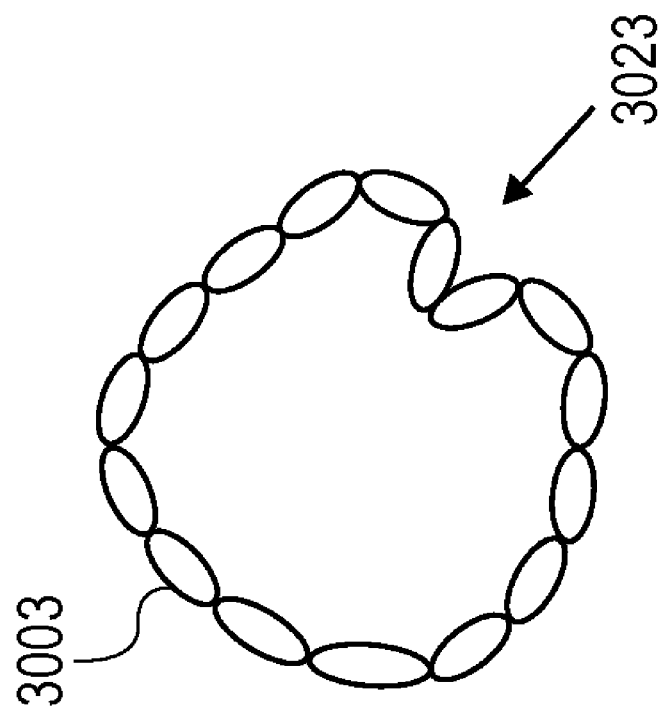

In use, the inflatable balloon elements may be expanded to open the partitioning device. For example, upon inflation, the inflatable elements may push the expansion of the struts of the device, thereby encouraging radial expansion of the membrane. The inflatable balloon elements may also be configured to accommodate non-circular deployment within the ventricle. FIGS. 30C and 30D illustrate different variations of partitioning devices including inflatable balloon elements that may conform to non-circular (or otherwise irregular) walls of the heart. For example, in FIG. 30C, the plurality of inflatable elements shown 3003 may be inflated so that they provide outward (axially) force to expand the device, and also to seal the device against the ventricle wall, but the plurality of inflatable elements also accommodate irregularities because the size of the sub-regions that include an inflatable balloon element may be displaced without disrupting the rest of the membrane. In FIG. 30C, one region of the partitioning device 3023 is allowed to follow a contour of the heart wall that is not round. For example, where trabeculations or other projections in the ventricle wall make it irregular. Similarly, when the body region (e.g., ventricle) is not rounded but is oval or otherwise non-circular, the inflatable balloon elements as shown in FIG. 30D may allow it to conform to the walls.

In some variations, an inflatable balloon may be included in the partitioning device that is not located on or near the periphery of the membrane. For example, FIGS. 31A and 31B illustrate one variation in which the central region of the implant (e.g. near the hub) on the membrane is inflatable, and inflation may help rapidly expand the partitioning device.

Figure 31A:
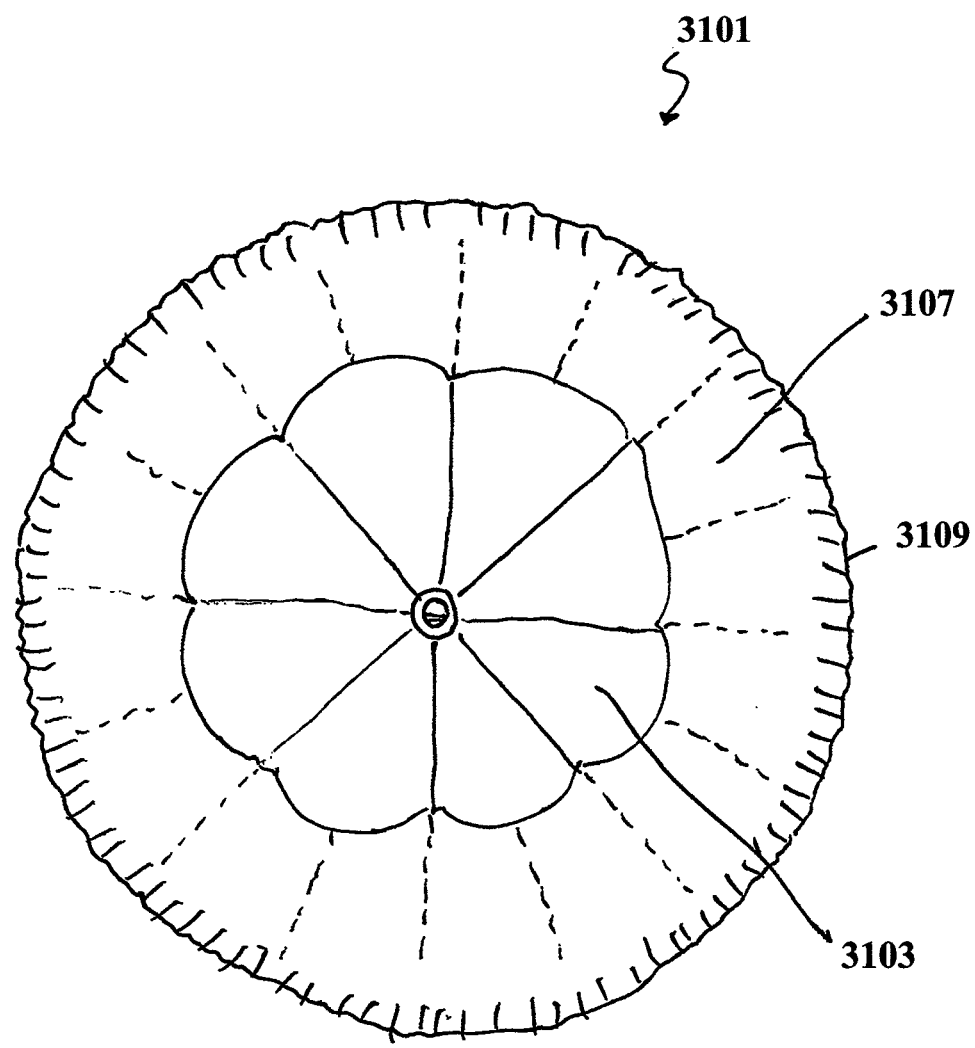
FIGS. 31A and 31B show another variation of a partitioning device including an inflatable element that may be used to expand the device.
Figure 31B:
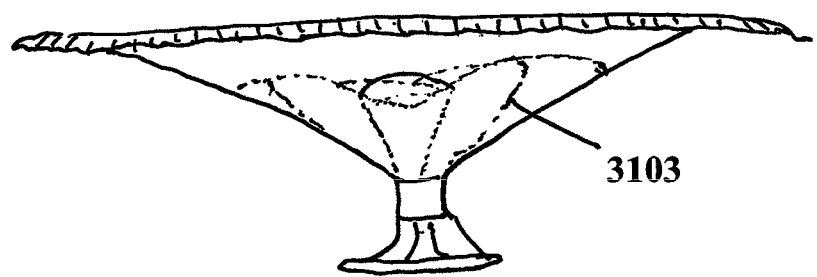

For example, in FIG. 31A, the partitioning device 3101 includes one or more inflatable regions 3103 that are located on the membrane 3107. These inflatable region or regions may also be formed between two of the layers forming the membrane, as mentioned above. For example, two layers of ePTFE forming the membrane may be sealed near the outer periphery 3109 of the device, but allowed to be separate closer to the hub, so that this region may be inflated. A port or ports for inflation (including or more valves) may also be included. In addition to the inflatable elements shown in FIG. 31A, other variations may also include one or more other sealing elements (e.g., a strand, a peripheral inflatable element, etc.) for helping to secure the membrane to the ventricle walls. In some variations the edges of the membrane may also be loose, serrated, etc., so as to help form a seal.

The partitioning device of FIG. 30A is shown in partially transparent side-view in FIG. 30B. In this example, the inflatable elements 3103 (which may also be referred to as inflatable expanding elements or inflatable expanding balloon elements) are indicated. Although these elements may drive the membrane open and towards the wall of the ventricle, they are not necessarily sealing elements, since they do not necessarily tension the membrane (e.g., removing wrinkles) to seal, in contrast to the device shown in FIG. 30A-30D. They may be used in combination with other sealing elements, as mentioned.

Figure 22A:
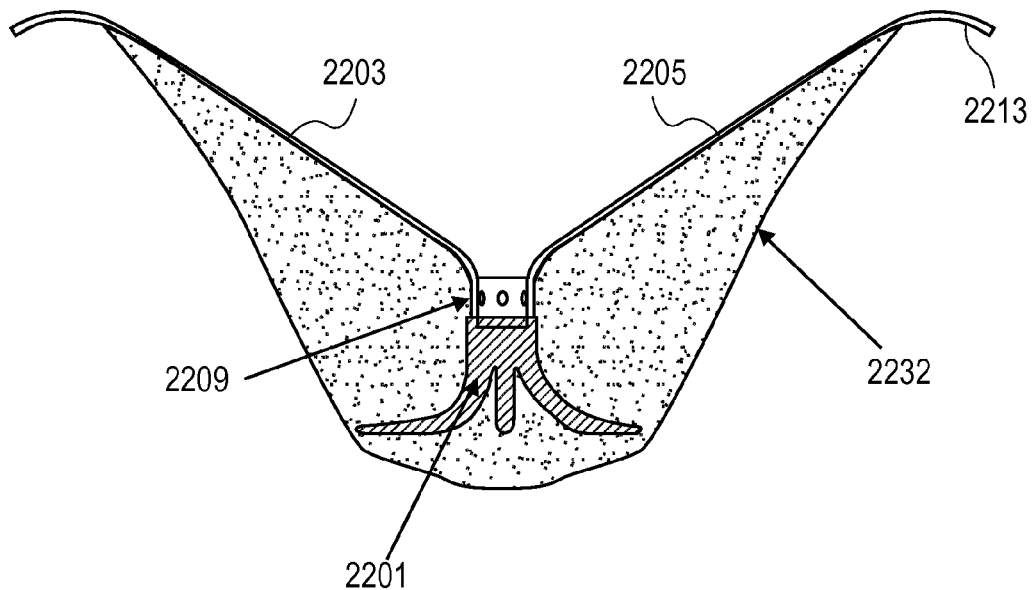
FIGS. 22A and 22B show a partitioning device having a container configured to be positioned within the non-productive portion of a ventricle when the device is delivered to a ventricular chamber, as illustrated in FIG. 22B.
Figure 22B:
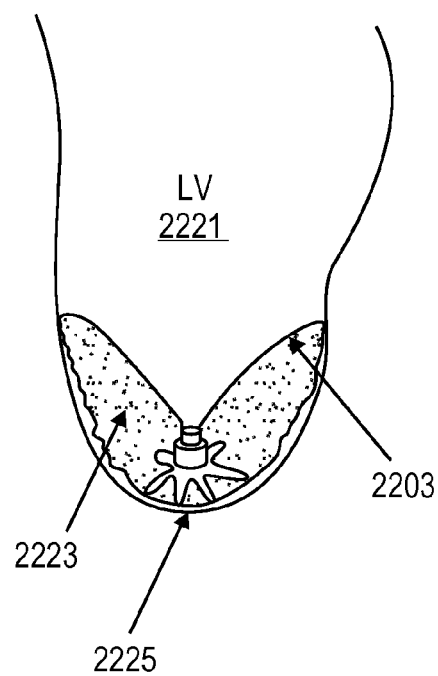

FIGS. 22A-25B illustrate variations of the devices including a container surrounding a portion of the partitioning device, and configured to be positioned within the non-productive portion of the heart chamber when the device is deployed in a heart chamber. For example, FIG. 22A shows a cross-section through one variation of a partitioning device in which the implant includes a frame of ribs or struts 2203 and a membrane connected to the frame 2205. One or more passive anchors (e.g., prongs, hooks, etc.) 2213 may be located on the ends of each strut. In this example, the membrane is formed of ePTE, and may be laminated over the frame to form the pressure-receiving surface of the device. The implant also includes a foot 2207 that is relatively soft (e.g., atraumatic) so that it doesn't penetrate the tissue wall, even when the wall may be weakened or akinetic. In this example, the device also includes a container 2232 formed by the pressure-receiving membrane and a second membrane (e.g., an ePTFE membrane) extending distally around the portion of the device that will be positioned within the non-productive portion of the membrane, as illustrated in FIG. 22b. In FIGS. 22A and 22B the container is configured as a bag, the top of which is sealed by the pressure-receiving membrane 2205. The device may include one or more ports 2209 (which may include valves) for filling the container. In FIG. 22A, the ports are configured as skives 2209 through which material may be injected to fill the container. FIG. 22B illustrates the device of FIG. 22A implanted into a ventricle (a left ventricle 2221). In this example, saline 2223 has been injected to fill the container, which contacts the wall of the apex region 2225 of the left ventricle 2221.

Figure 23A:
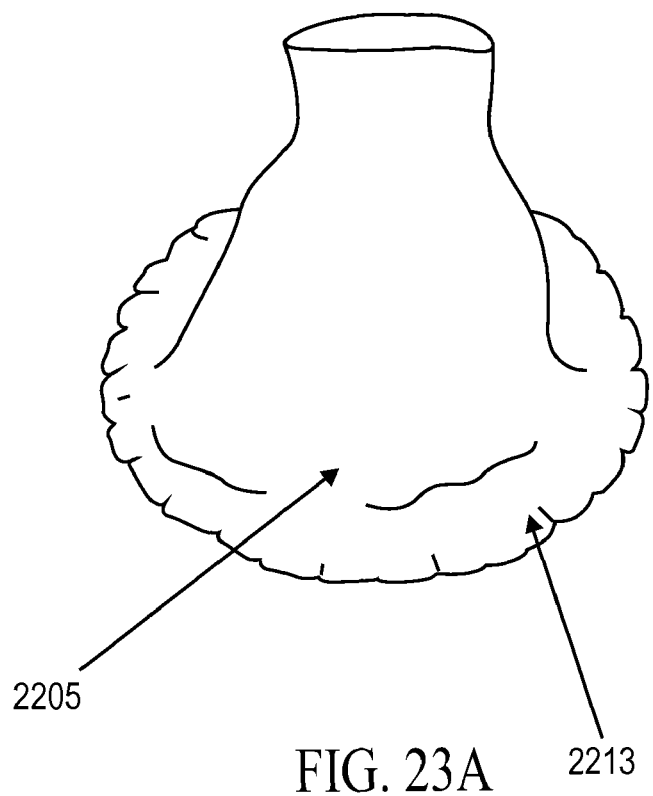
FIGS. 23A and 23B, respectively, show a bottom and side perspective view of another variation of a partitioning device including a container portion.
Figure 23B:
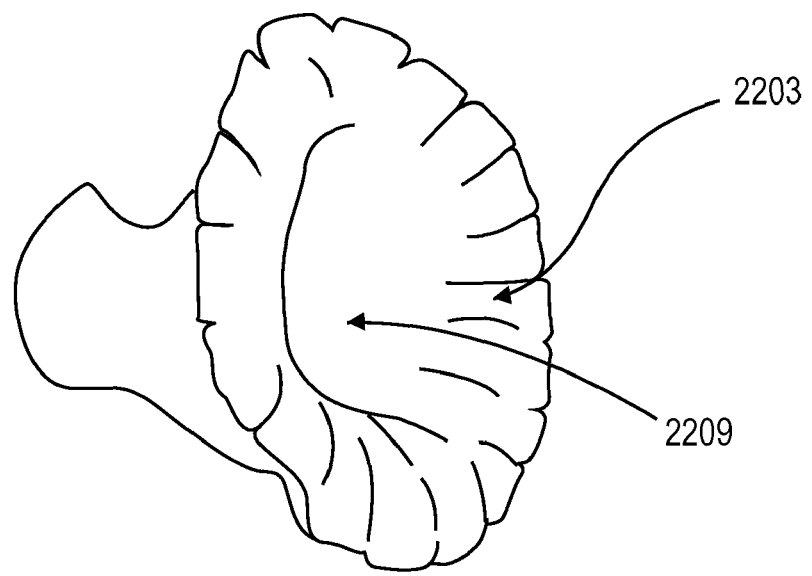

FIG. 23A and 23B show perspective views of a similar variation.

Figure 24A:
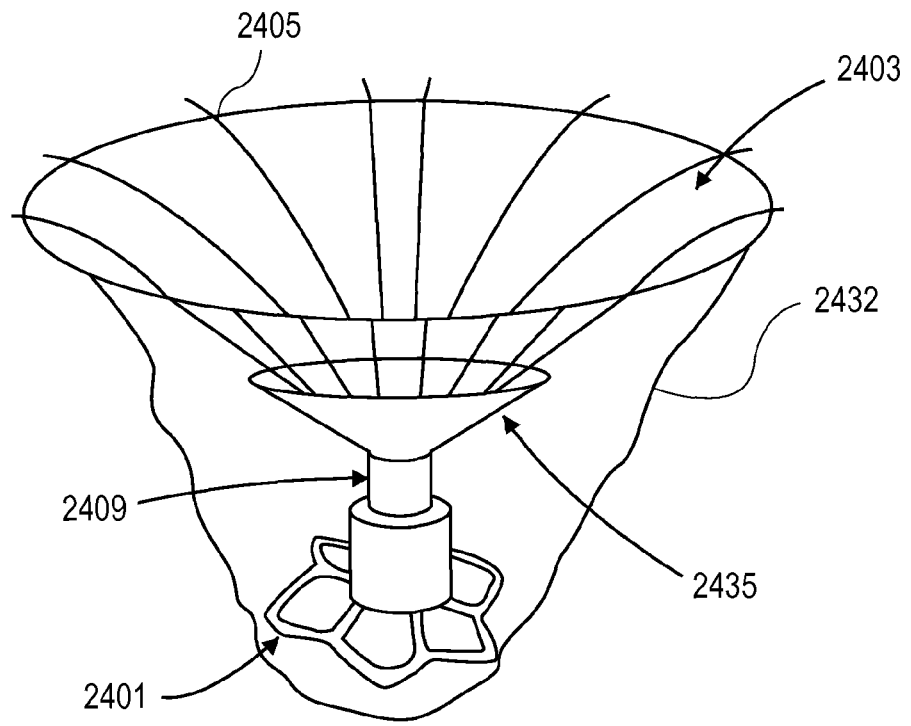
FIGS. 24A and 24B show side perspective and top views, respectively of another variation of a partitioning device having both a container and a valved port for filling the container.

FIG. 24A is another example of a portioning device that includes an occlusive membrane 2403 secured to a plurality of ribs or struts 2405. The device also includes a container 2432 which, similar to the variation shown in FIGS. 22A-23B, is an inflatable bag-like structure formed of ePTFE. The example shown in FIG. 24A also includes a valve, configured as a flap valve, 2435, which is a membrane of ePTFE that covers openings (e.g., skives) through which the container may be filled. The membrane may be biased (e.g., by the elastic structure of the valve, and/or by pressure from within the container) so that it opens for filling, but does not permit a significant amount of material to leave the container. Thus the container may be filled through the implant hub 2409. For example, the container may be filled using the delivery catheter (not shown). The hub portion 2409 and an atraumatic foot region 2401 are shown positioned within the container. In some variations, the container may surround the foot region and/or the hub, but not enclose them.

Figure 24B:
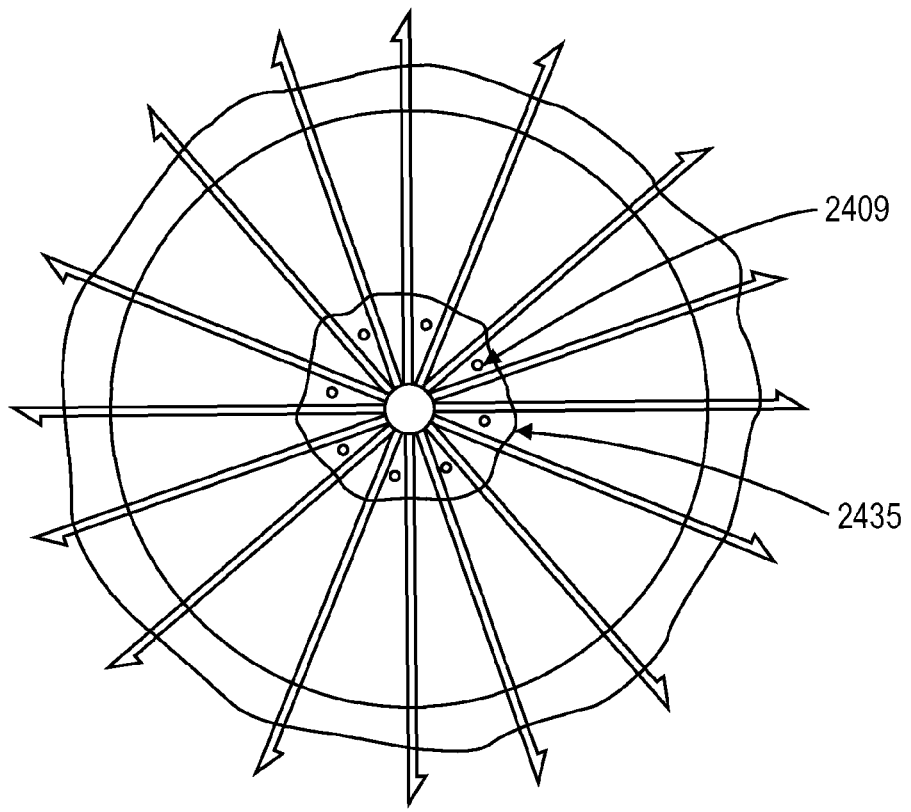
Figure 25A:
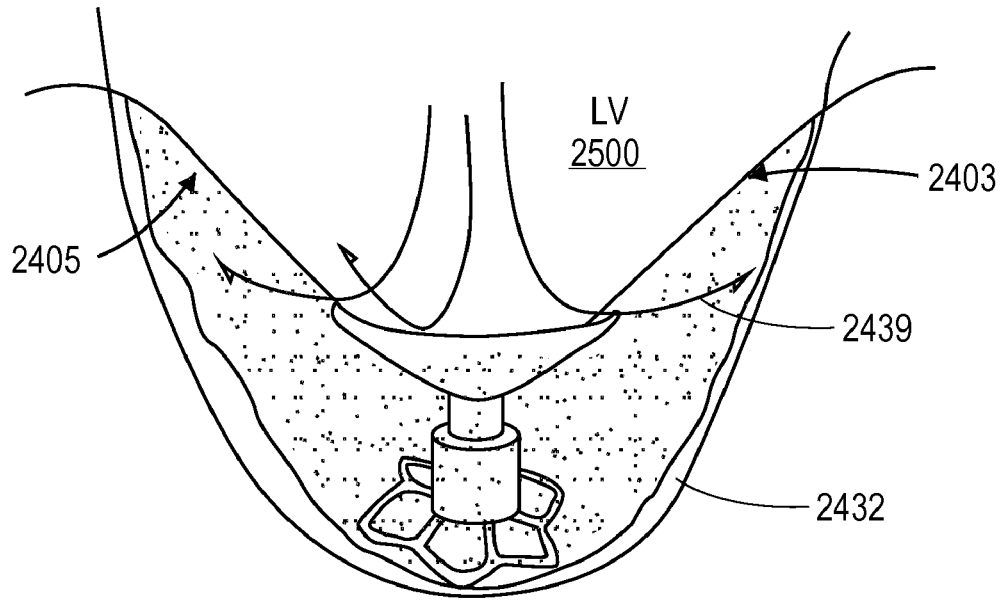
FIGS. 25A and 25B illustrate operation of a partitioning device similar to that shown in FIGS. 24A and 24B.
Figure 25B:
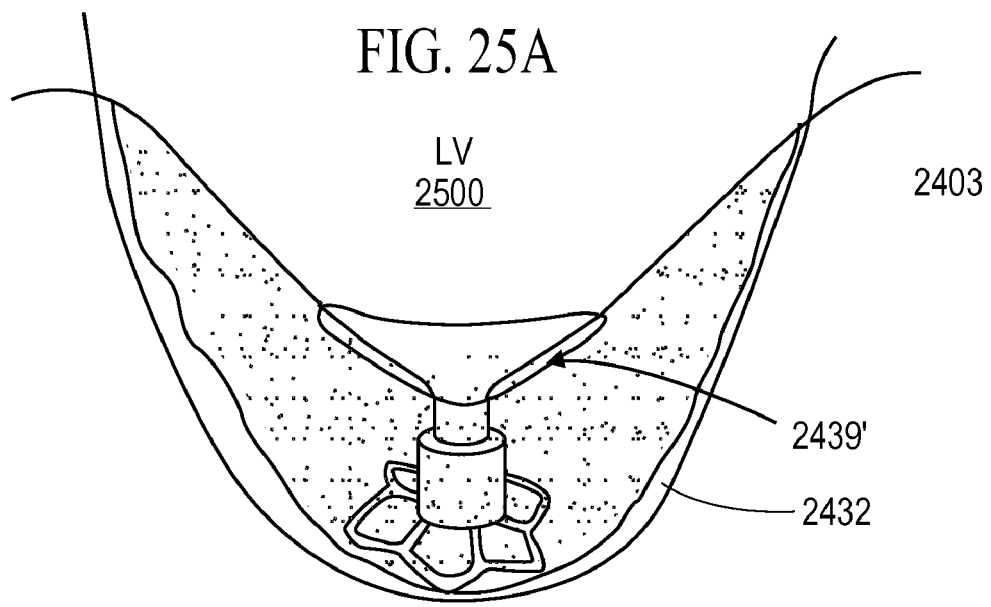

FIG. 24B shows a top view of the device of FIG. 24A, illustrating the openings 2409 (skives) into the container that are selectively covered by the flap valve 2435. These openings may also be configured so that fluid, such as blood from within the ventricle, can be loaded into the chamber once it is positioned. An example of this is shown in FIGS. 25A and 25B. In this example, the device is shown expanded within a ventricle 2500. The flap valve allows blood (e.g., blood being pumped through the ventricle) to enter the container 2432, as indicated by the arrows 2439. This may inflate the container within the ventricle, so that the walls of the container conform to the wall of the non-productive region of the ventricle, i.e., the region behind the partitioning membrane 2403 and ribs 2405. For example, during the period of contraction of the ventricle when blood is pushed against the pressure-receiving membrane of the device as the ventricle fills (e.g., diastole), blood may enter and fill the chamber. When the ventricle contracts (e.g., systole), blood is held in the chamber since the flap valve is configured to prevent blood from leaving the chamber. After the chamber is filled, blood may be held within the chamber and prevented from exiting the chamber by the flap valve, as indicated by the arrows 2439' in FIG. 25B. Thus, this variation may be self-filling.

Figure 26:
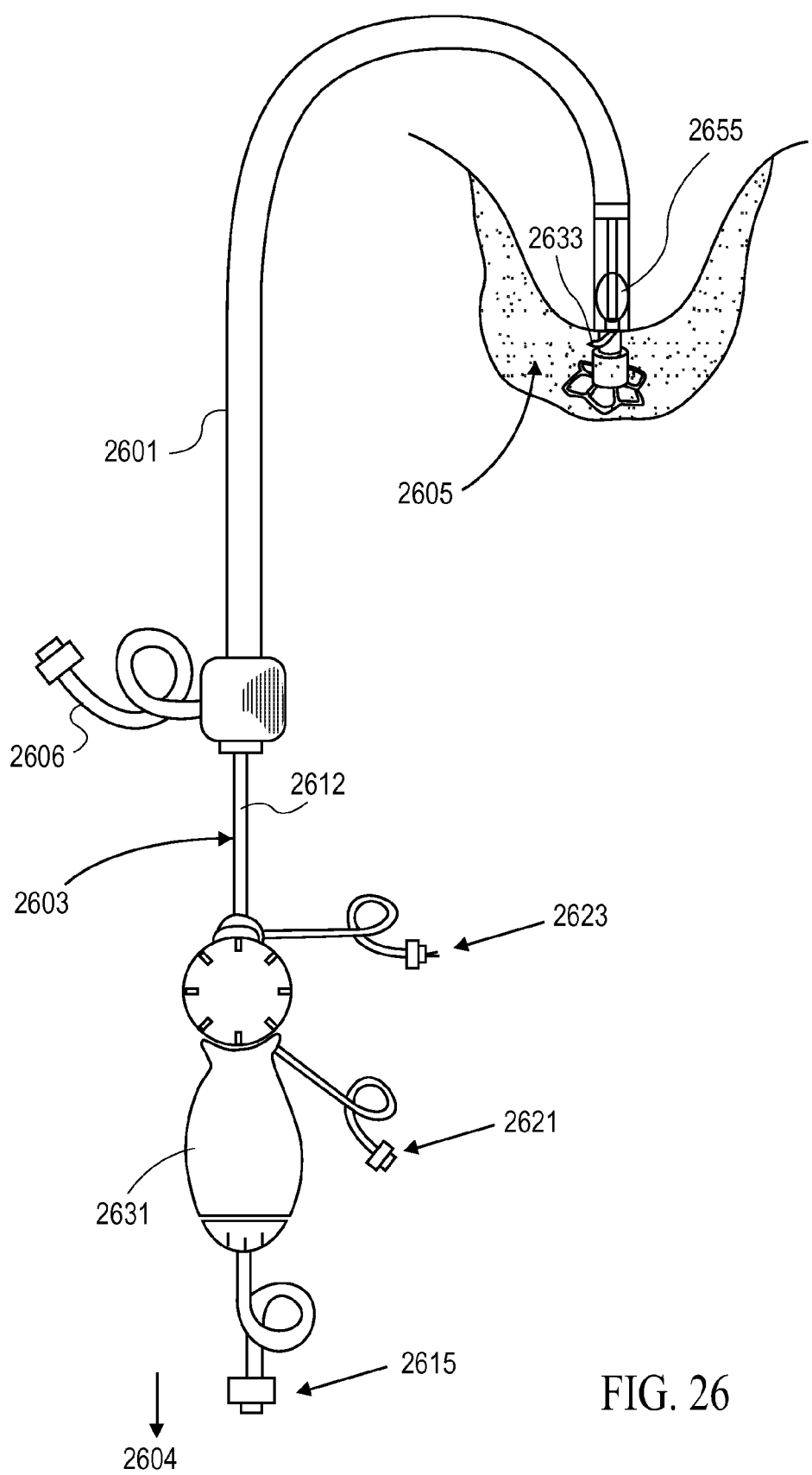
FIG. 26 shows a delivery catheter for a partitioning device having a valved container.

FIG. 26 illustrates one variation of an applicator that may be used with a partitioning device such as the partitioning devices including chambers illustrated above. In FIG. 26, the applicator is a delivery catheter 2603 that may be used with a guide catheter 2601. The guide catheter 2601 in this example has an inner lumen extending between the proximal end 2604 and distal end. A hemostatic valve (not shown) may be provided at the proximal end 2604 of the guide catheter 2601 to seal about the outer shaft of the delivery catheter 2602. In this example, the guide catheter also includes a flush port 2606 on the proximal end 2604 of guide catheter 2601 that is in fluid communication with the inner lumen.

The applicator delivery catheter 2603 ("applicator") has an elongated outer shaft 2612 with an inflation port (e.g., deployment inflation port 2615) near the proximal end. The inflation port may be used to inflate an inflatable member on the distal portion of the elongate shaft configured to help expand the device. This inflatable member may also be referred to as a deployment balloon 2655. The deployment inflation port is in communication with an inner lumen in the delivery catheter and with a deployment balloon 2655.

The applicator also includes a releaseable securing element as previously described, for releasably securing the implant device. For example, the releasable securing element may include a torque shaft and helical coil screw as illustrated and described in FIG. 8, above.

The applicator may also include a filling interface 2621 near the distal end of the elongate shaft for filling the non-productive portion of the heart formed by the implant. In some variations, the filling interface may be configured as an inflation port for inflating or filling a container portion of the implant. The filling interface may be configured as a filling port, and may be used to fill the non-productive region after the implant has been deployed even if the implant does not include a container portion.

The system shown in FIG. 26 (including a delivery catheter or applicator 2603, insertion catheter 2601, and expandable partitioning device 2605) may also be configured for use with a UV-curable filling material. In this variation, the applicator also includes a light-emitting element such as a fiber optic cable 2633 near the distal end, and a port 2623 for an energy source near the proximal end, so that energy (e.g., Uv-light) can be used to cure the filler in the non-productive region and/or the container 2605.

The applicator may also include a handle 2621 at or near the proximal end.

Figure 27:
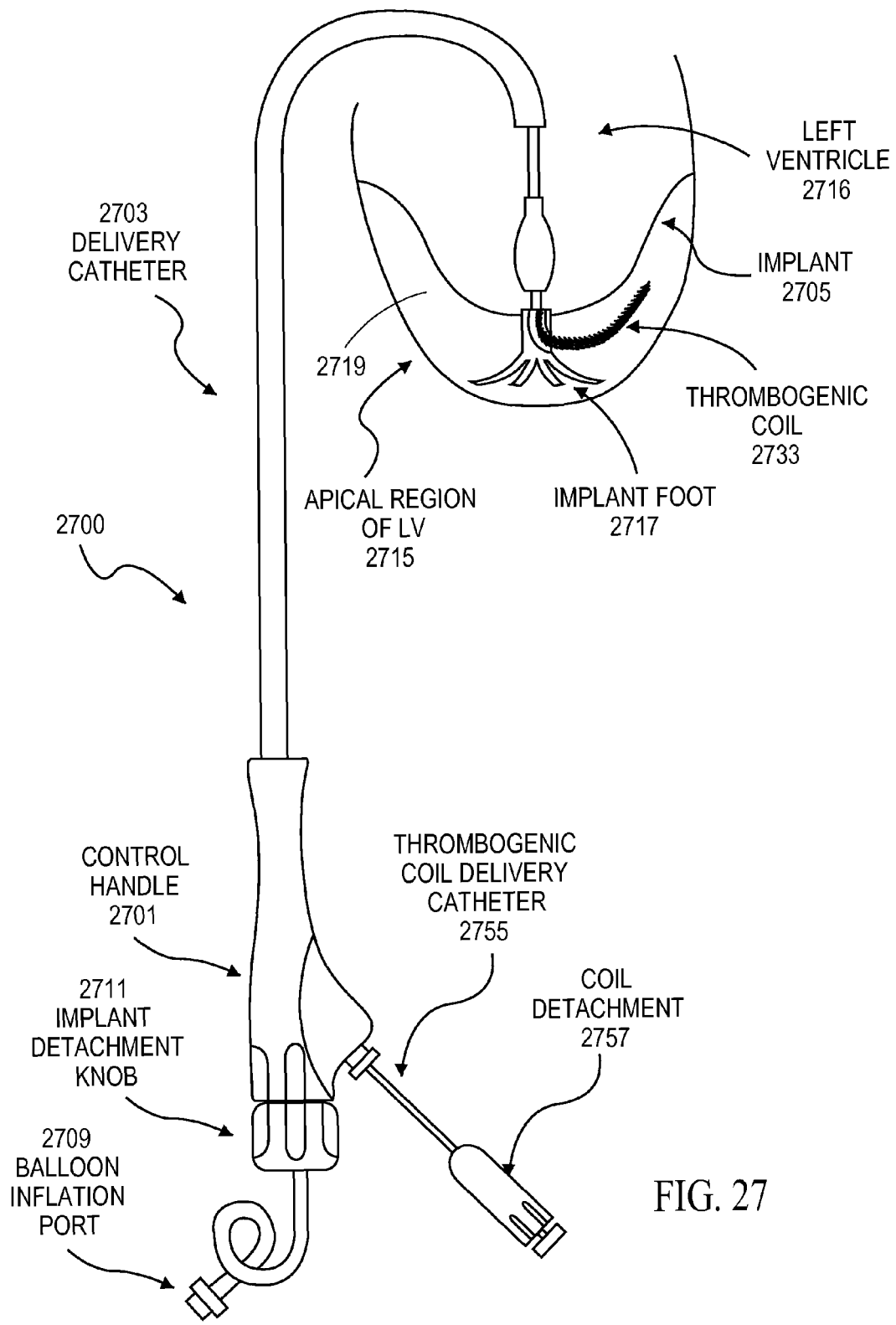
FIG. 27 illustrates operation of a delivery catheter similar to the delivery catheter shown in FIG. 26.

FIG. 27 illustrates another variation of a system including a partitioning device 2705, and an applicator that is configured to deploy a partitioning device and then deliver occlusive members (e.g., coils) into the non-productive portion formed behind the device. For example, in this variation the applicator 2700 includes a control handle 2701 and a balloon deployment inflation port 2709 at the proximal end, as well as an implant detachment knob 2711. Turning the implant detachment knob may rotate the torque shaft (not visible) and deploy the implant, as previously described. The system may also include a delivery catheter 2703.

In FIG. 27, the partitioning device 2705 is shown deployed within the apical region of a left ventricle 2715 so that the foot 2717 of the device rests against the wall and the pressure-receiving membrane forms a non-productive region 2719 separate from the productive region of the ventricle 2716. The membrane may be reinforced with ribs or struts, and may be anchored via one or more securing elements (not visible in this example).

In this variation, the applicator may also be used to apply occlusive elements into the non-productive region 2719. As illustrated the occlusive elements are coils, e.g., thrombogenic coils 2733). Thus, the applicator may include a port and passageway for the occlusive member. For example, the applicator may include a coil delivery catheter 2755, and may also include a coil detachment knob 2757. In operation, the coils may be delivered behind the expanded implant by pushing the coils out of the distal end from behind the deployed partitioning device until this region is filled as desired. The coil may then be detached, although multiple small coils may also be used. Any occlusive material may be used, including any variation of occlusive coil. For example, thrombogenic coils may be used in the non-productive portion.

Figure 28:
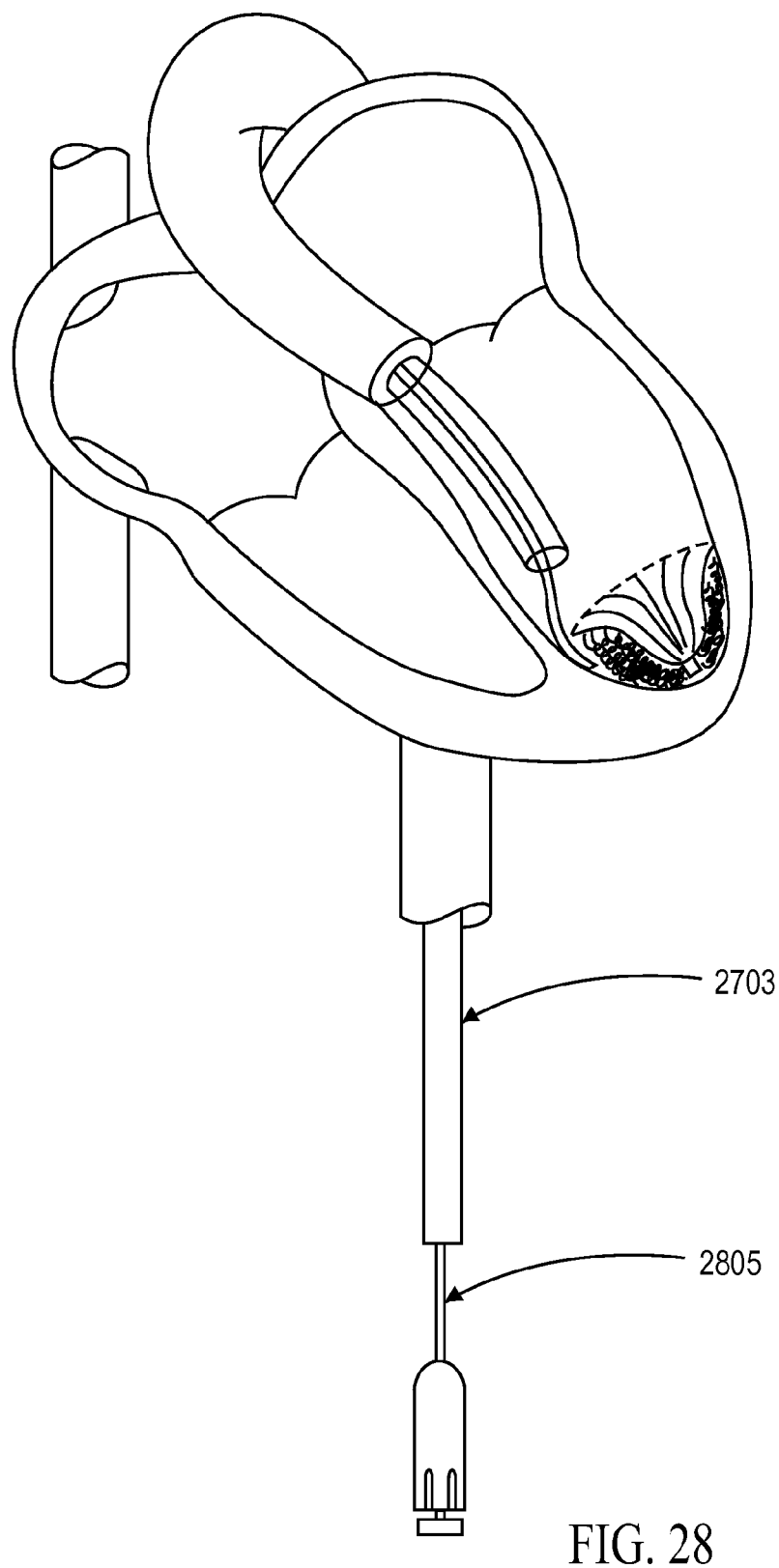
FIG. 28 illustrates one method of implanting a partitioning device as described herein.

FIG. 28 illustrates another variation of a partitioning device that can be filled with an occlusive material such as a thrombogenic coil. In this variation the non-productive portion is filled after the device has been deployed using a separate coil delivery device 2805. The coil delivery device (e.g., coil delivery catheter) may be used with the same guide catheter 2703 used to by the applicator to position and deploy the implant. The coil delivery catheter may be used to fill the region behind the device by filling from an edge of the device, by separating the edge of the membrane of the device from the wall of the heart to allow the distal end of the coil delivery device into the non-productive space.

Figure 29A:
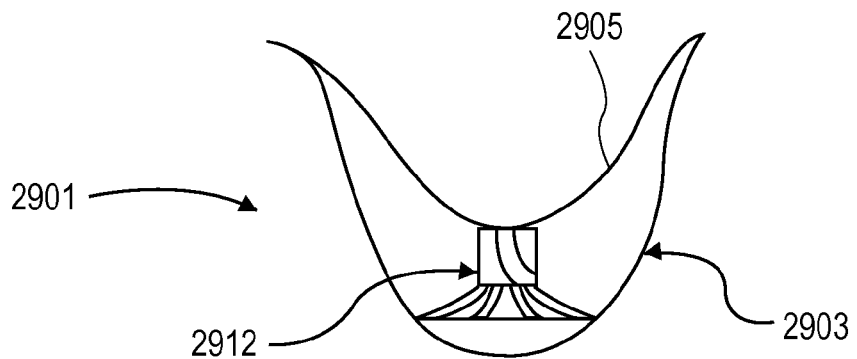
FIGS. 29A and 29B illustrate another variation of a method of using a partitioning implant.
Figure 29B:
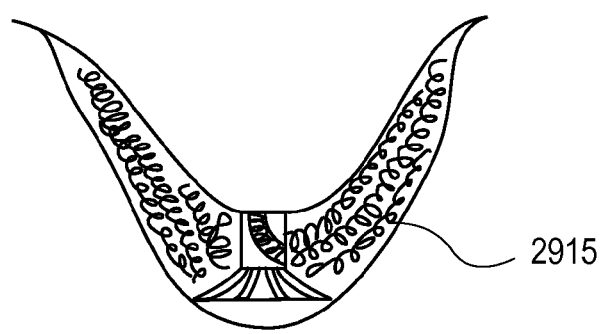
Figure 29C:
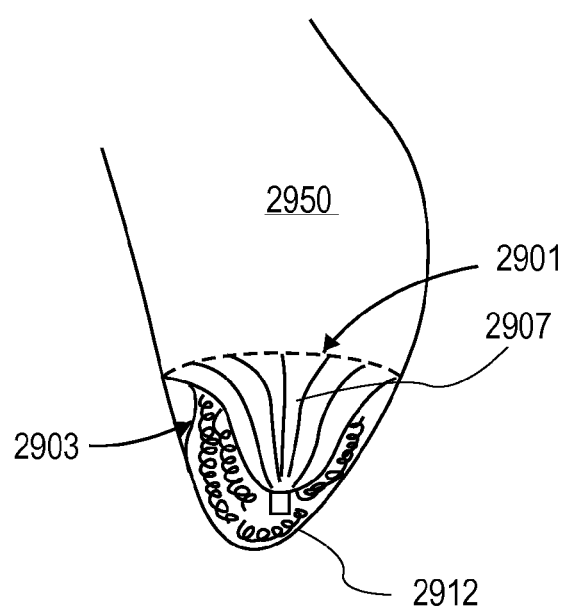
FIG. 29C illustrates an alternative method of operating a portioning device similar to the version shown in FIG. 29B.

FIGS. 29A-29C illustrate another variation of the method of filling a portion of the non-productive region formed by a partitioning device 2901 with an occlusive material(s) such as occlusive coils. FIG. 29A illustrates one variation of a partitioning device 2901 that includes a container 2903 configured as a pouch or bag that is bounded on at least one side by the pressure receiving membrane 2905. The pressure-receiving membrane 2905 may be supported by struts 2907. In some variations the container is not bounded by the pressure-receiving membrane. The implant foot 2912 is within the container (which may also be referred to as a bag or pouch).

In operation the device may be deployed in a heart chamber (e.g., the left ventricle 2950) and the container may be filled with occlusive material. For example, FIG. 29B illustrates the partitioning device of FIG. 29A filled with occlusive coils 2915. When the device is secured within the heart, as illustrated in FIG. 29C, the container may be filled so that virtually the entire non-productive portion is filled (by the filled container).

While particular forms of the invention have been illustrated and described herein, it will be apparent that various modifications and improvements can be made to the invention. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is intended that this invention to be defined by the scope of the appended claims as broadly as the prior art will permit.

As used herein, terms such a "element", "member", "component", "device", "section", "portion", "step", "means" and words of similar import, shall not be construed as invoking the provisions of 35 U.S.C. .sctn. 112(6) unless the following claims expressly use the term "means" followed by a particular function without specific structure or the term "step" followed by a particular function without specific action. Accordingly, it is not intended that the invention be limited, except as by the appended claims. All patents and patent applications referred to herein are hereby incorporated by reference in their entirety.

What is claimed is:

1. A device for partitioning a patient's ventricle into a productive portion and a non-productive portion, the device comprising:
   a membrane and a membrane support frame sized to span the patient's ventricle, wherein the membrane support frame comprises a plurality of support struts configured to have a collapsed and an expanded configuration;
   at least one securing element extending from the periphery of the membrane; and
   an inflatable sealing element on a peripheral portion of the membrane configured to seal the peripheral portion of the membrane to a wall of the ventricle.

2. The device of claim 1, wherein the inflatable sealing element extends substantially around the perimeter of the membrane.

3. The device of claim 1, further comprising a plurality of inflatable sealing elements around the perimeter of the membrane.

4. The device of claim 1, further comprising an inflation port configured to connect the inflatable sealing element to a channel on a delivery device.

5. The device of claim 1, further comprising an inflation valve fluidly connected to the inflatable sealing element.

6. The device of claim 1, wherein the securing element has a tissue penetrating tip.

7. The device of claim 1, further comprising a container secured to the device and configured to be positioned within the non-productive portion of the subject's ventricle when the device is deployed in the patient's ventricle.

8. The device of claim 1, wherein the support frame comprises a hub and the plurality of support struts extend radially from the hub.

9. The device of claim 8, wherein the hub comprises a lumen having a proximal port located on a proximal portion of the hub and a distal port located on a distal portion of the hub, wherein the lumen is configured to provide access from the productive portion of the ventricle to the non-productive portion of the ventricle after deployment of the device within the ventricle.

10. The device of claim 1, wherein the inflatable sealing element is a balloon.

11. The device of claim 1, wherein the membrane comprises a first layer and a second layer with the inflatable sealing element disposed between the first layer and the second layer.

12. The device of claim 1, wherein one or more of the plurality of support struts is inflatable.

* * * * *

UNITED STATES PATENT AND TRADEMARK OFFICE
CERTIFICATE OF CORRECTION

PATENT NO. : 8,377,114 B2  
APPLICATION NO. : 12/422177  
DATED : February 19, 2013  
INVENTOR(S) : Khairkhahan et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 873 days.

Signed and Sealed this  
Twentieth Day of August, 2013

Teresa Stanek Rea  
*Acting Director of the United States Patent and Trademark Office*